United States Patent

Venet et al.

[11] Patent Number: 6,124,330
[45] Date of Patent: Sep. 26, 2000

[54] N-[4-(HETEROARYLMETHYL)PHENYL]-HETEROARYLAMINES

[75] Inventors: Marc Gaston Venet, Le Mesnil Esnard; Dominique Jean-Pierre Mabire, La Saussaye; Jean Fernand Armand Lacrampe; Gerard Charles Sanz, both of Le Mesnil Esnard, all of France

[73] Assignee: Janssen-Cilag S.A., Issy-les-Moulineaux Cedex, France

[21] Appl. No.: 09/214,080

[22] PCT Filed: Jun. 19, 1997

[86] PCT No.: PCT/EP97/03248

§ 371 Date: Apr. 29, 1999

§ 102(e) Date: Apr. 29, 1999

[87] PCT Pub. No.: WO97/49704

PCT Pub. Date: Dec. 31, 1997

[30] Foreign Application Priority Data

Jun. 27, 1996 [EP] European Pat. Off. .............. 96201781

[51] Int. Cl.[7] .................... A61K 31/426; A61P 17/06; C07D 277/22; C07D 277/60; C07D 417/10

[52] U.S. Cl. .................... 514/365; 514/367; 514/370; 514/372; 514/373; 514/231.5; 514/233.8; 514/235.2; 514/235.5; 514/235.8; 514/236.8; 514/252.13; 514/254.01; 514/254.04; 514/315; 514/323; 514/324; 514/326; 548/152; 548/190; 548/206; 548/208; 548/212; 548/214; 546/197; 546/198; 546/202; 546/208; 546/209; 546/229; 544/133; 544/135; 544/139; 544/141; 544/367; 544/368; 544/369; 544/370; 544/372; 540/602; 540/603

[58] Field of Search ...................................... 514/365, 367, 514/370, 372, 373; 548/152, 190, 206, 208, 212, 214

[56] References Cited

FOREIGN PATENT DOCUMENTS

| 0 260 744 A2 | 3/1988 | European Pat. Off. . |
| 0 260 744 A3 | 3/1988 | European Pat. Off. . |
| 0 371 559 A2 | 6/1990 | European Pat. Off. . |

*Primary Examiner*—Joseph McKane
*Assistant Examiner*—Jane C. Oswecki

[57] ABSTRACT

The present invention is concerned with compounds of formula

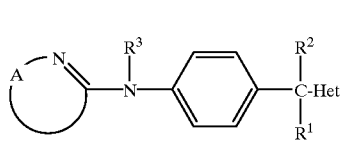

(I)

the N-oxides, the pharmaceutically acceptable addition salts and the stereochemically isomeric forms thereof, wherein $R^1$ is hydrogen, hydroxy, $C_{1-6}$alkyl or aryl; $R^2$ is hydrogen; optionally substituted $C_{1-12}$alkyl; $C_{3-7}$cycloalkyl; $C_{2-8}$alkenyl, optionally substituted pyrrolidinyl or aryl; $R^3$ is hydrogen, optionally substituted $C_{1-6}$alkyl or aryl; Het is an optionally substituted unsaturated heterocycle selected from imidazolyl, triazolyl, tetrazolyl and pyridinyl;

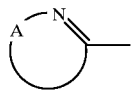

is an optionally substituted unsaturated mono- or bicyclic heterocycle; and aryl is optionally substituted phenyl. The present invention also relates to processes for their preparation and compositions comprising said new compounds, as well as their use as a medicine.

12 Claims, No Drawings

N-[4-(HETEROARYLMETHYL)PHENYL]-HETEROARYLAMINES

CROSS REFERENCE TO RELATED APPLICATIONS

This application is a National Stage application under 35 U.S.C. § 371 of PCT/EP97/03248 filed Jun. 19, 1997, which claims priority from EP 96.201.781.0, filed Jun. 27, 1996.

The present invention concerns N-[4-(heteroaryl-methyl)phenyl]-heteroarylamines, their N-oxides and addition salts; it further relates to processes for their preparation, and compositions comprising them. The compounds of the present invention are potent inhibitors of the retinoic acid-metabolism, and hence, their use as a medicine is also described.

EP-A-0,260,744, published on Mar. 23, 1988, discloses (1H-imidazol-1-ylmethyl) substituted benzimidazoles as inhibitors of the androgen formation from $C_{21}$-steroids, as inhibitors of the biosynthesis of thromboxane $A_2$, and also having the capability to increase the excretion of ureic acid. EP-A-0,371,559, published on Jun. 6, 1990, discloses said benzimidazoles and analogous benzotriazoles as potent suppressors of the plasma elimination of endogenously or exogenously administered retinoic acid.

Retinoic acid (RA) is a key molecule in the regulation of growth and differentiation of epithelial tissues. However, RA is very rapidly metabolized by a series of enzymatic reactions, which results in its deactivation. Inhibition of RA-metabolism leads to enhanced RA levels in plasma and tissue. Therefore, compounds with such an inhibitory action, also called retinoic mimetic activity, have therapeutic and/or preventive potential in the field of dermatology and oncology.

The novel compounds of the present invention have retinoic mimetic activity and, moreover, show little or no endocrinological side-effects.

The present invention is concerned with compounds of formula

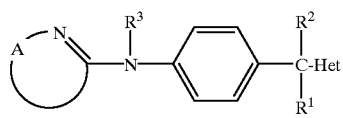

(I)

the N-oxides, the pharmaceutically acceptable addition salts and the stereochemically isomeric forms thereof, wherein:

$R^1$ represents hydrogen, hydroxy, $C_{1-6}$alkyl or aryl;

$R^2$ represents hydrogen; $C_{1-12}$alkyl; $C_{3-7}$cycloalkyl; $C_{2-8}$alkenyl; aryl; pyrrolidinyl optionally substituted with $C_{1-4}$alkyl or $C_{1-4}$alkyloxycarbonyl; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- and di(aryl)-amino, arylC$_{1-4}$ alkylamino, ($C_{1-4}$alkyl)(arylC$_{1-4}$alkyl)amino, pyrrolidinyl, piperidinyl, piperazinyl optionally substituted with $C_{1-4}$alkyl, morpholinyl, perhydroazepinyl, carboxyl, $C_{1-4}$alkyloxycarbonyl, aminocarbonyl, mono- and di($C_{1-4}$alkyl)aminocarbonyl, aryl, aryloxy and arylthio;

$R^3$ represents hydrogen, $C_{1-6}$alkyl, aryl or $C_{1-6}$alkyl substituted with aryl;

Het represents an unsaturated heterocycle selected from imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl;

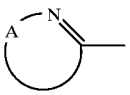

represents an unsaturated mono- or bicyclic heterocycle selected from the group consisting of pyridinyl, pyridazinyl, pyrimidinyl, pyrazinyl, quinolinyl, isoquinolinyl, purinyl, phtalazinyl, cinnolinyl, quinazolinyl and quinoxalinyl; each of said unsaturated mono- or bicyclic heterocycles may optionally be substituted with one, two or three substituents selected from hydroxy, halo, nitro, amino, $C_{1-6}$alkyl, hydroxyC$_{1-6}$alkyl, haloC$_{1-6}$alkyl, $C_{1-6}$alkyloxy, $C_{1-6}$alkylthio, formyl, carboxyl, mono- or di($C_{1-6}$alkyl)amino, $C_{1-6}$alkyloxycarbonyl or aryl; or

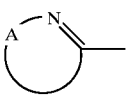

represents a radical of formula

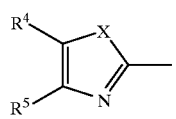

(a)

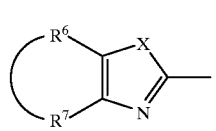

(b)

wherein:

each X independently represents $NR^8$, O, S, S($=$O) or S($=$O)$_2$; wherein $R^8$ is hydrogen, $C_{1-6}$alkyl, aryl or arylC$_{1-6}$alkyl;

$R^4$ and $R^5$ each independently represent hydrogen, hydroxy, halo, cyano, nitro, amino, $C_{1-6}$alkyl, hydroxyC$_{1-6}$alkyl, haloC$_{1-6}$alkyl, $C_{1-6}$alkyloxy, formyl, carboxyl, mono- or di($C_{1-6}$alkyl)amino, $C_{1-6}$alkyloxycarbonyl or aryl;

—$R^6$—$R^7$— represents a bivalent radical of formula:

| | |
|---|---|
| —$CR^9$=$CR^9$—$CR^9$=$CR^9$— | (b-1); |
| —N=$CR^9$—$CR^9$=$CR^9$— | (b-2); |
| —$CR^9$=N—$CR^9$=$CR^9$— | (b-3); |
| —$CR^9$=$CR^9$—N=$CR^9$— | (b-4); |
| —$CR^9$=$CR^9$—$CR^9$=N— | (b-5); |
| —$CR^9$=N—N=$CR^9$— | (b-6); |
| —$CR^9$—N—$CR^9$=N— | (b-7); |
| —$CR^9$=$CR^9$—N=N— | (b-8); |
| —N=N—$CR^9$=$CR^9$— | (b-9); |
| —N=$CR^9$—N=$CR^9$— | (b-10); |
| —N=$CR^9$—$CR^9$=N— | (b-11); |
| —$CR^9$=N—N=N— | (b-12); |
| —N=$CR^9$—N=N— | (b-13); |
| —N=N—$CR^9$=N— | (b-14) or |
| —N=N—N=$CR^9$— | (b-15); | wherein each $R^9$ independently represents hydrogen, hydroxy, halo, nitro, amino, $C_{1-6}$alkyl, hydroxyC$_{1-}$ 6alkyl, haloC$_{1-6}$alkyl, C$_{1-6}$alkyloxy, formyl, carboxyl, mono- or di(C$_{1-6}$alkyl)amino, C$_{1-6}$alkyloxy-carbonyl or aryl; and aryl represents phenyl or phenyl substituted with one, two or three substituents selected from hydroxy, halo, cyano, amino, mono- or di(C$_{1-6}$alkyl)amino, C$_{1-6}$alkyl, haloC$_{1-6}$alkyl, hydroxyC$_{1-6}$alkyl, C$_{1-6}$alkyloxy, formyl, carboxyl and C$_{1-6}$alkylcarbonyl; or two adjacent carbon atoms on said phenyl may be substituted by a single bivalent radical having the formula C$_{1-12}$alkanediyl or haloC$_{1-12}$alkanediyl.

As used in the foregoing definitions and hereinafter, halo is generic to fluoro, chloro, bromo and iodo; C$_{3-7}$cycloalkyl is generic to cyclopropyl, cyclobutyl, cyclopentyl, cyclohexyl and cycloheptyl; C$_{2-8}$alkenyl defines straight and branch chained hydrocarbon radicals containing one double bond and having from 2 to 8 carbon atoms such as, for example, ethenyl, 1-propenyl, 2-butenyl, 2-pentenyl, 3-pentenyl, 3-methyl-2-butenyl, 3-hexenyl, 3-heptenyl, 2-octenyl and the like; C$_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; C$_{1-6}$alkyl is meant to include C$_{1-4}$alkyl and the higher homologues thereof having 5 or 6 carbon atoms such as, for example, pentyl, 2-methylbutyl, hexyl, 2-methylpentyl and the like; C$_{1-12}$alkyl is meant to include C$_{1-6}$alkyl and the higher homologues thereof having from 7 to 12 carbon atoms such as, for example, heptyl, octyl, nonyl, decyl, undecyl, dodecyl, 2-methylhexyl, 3-ethyloctyl and the like; C$_{1-12}$alkanediyl defines bivalent straight and branched chain saturated hydrocarbon radicals having from 1 to 12 carbon atoms such as, for example, 1,1-methanediyl, 1,2-ethanediyl, 1,3-propanediyl, 1,4-butanediyl, 1,5-pentanediyl, 1,6hexanediyl, 1,2-propanediyl, 2,3-butanediyl, 1,7-heptanediyl, 1,8 octanediyl, 1,9-nonanediyl, 1,10-decanediyl, 1,11-undecanediyl, 1,12-dodecanediyl, 1,1,4,4-tetramethylbutane- 1,4-diyl and the like; haloC$_{1-6}$alkyl is defined as polyhalosubstituted C$_{1-6}$alkyl, in particular C$_{1-6}$alkyl substituted with 1 to 6 halogen atoms, more in particular difluoro- or trifluoromethyl; haloC$_{1-12}$alkanediyl is defined as polyhalosubstituted C$_{1-12}$alkanediyl, in particular C$_{1-12}$alkanediyl substituted with 1 to 12 halogen atoms; triazolyl is meant to include 1,2,4-triazolyl and 1,3,4-triazolyl; tetrazolyl is meant to include 1H-tetrazolyl and 2H-tetrazolyl.

The unsaturated heteroaryl group represented by Het may be attached to the remainder of the molecule of formula (I) through any ring carbon or heteroatom as appropriate. Thus, for example, when the heteroaryl group is imidazolyl, it may be a 1-imidazolyl, 2-imidazolyl, 4-imidazolyl and 5-imidazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl.

The pharmaceutically acceptable addition salts as mentioned hereinabove are meant to comprise the therapeutically active non-toxic base and acid addition salt forms which the compounds of formula (I) are able to form. The acid addition salt form of a compound of formula (I) that occurs in its free form as a base can be obtained by treating said free base form with an appropriate acid such as an inorganic acid, for example, hydrohalic acid, e.g. hydrochloric or hydrobromic, sulfuric, nitric, phosphoric and the like acids; or an organic acid, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) containing acidic protons may be converted into their therapeutically active non-toxic base, ie. metal or amine, addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted into the free forms by treatment with an appropriate base or acid.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I) are meant to comprise those compounds of formula (I) wherein one or several nitrogen atoms are oxidized to the so-called N-oxide.

The term "stereochemically isomeric forms" as used hereinbefore and hereinafter defines all the possible isomeric forms in which the compounds of formula (I) may occur. Unless otherwise mentioned or indicated, the chemical designation of compounds denotes the mixture, and in particular the racemic mixture, of all possible stereochemically isomeric forms, said mixtures containing all diastereomers and enantiomers of the basic molecular structure. Stereochemically isomeric forms of the compounds of formula (I) and mixtures of such forms are obviously intended to be encompassed by formula (I).

In particular, the compounds of formula (I) and some of the intermediates hereinafter have at least one stereogenic center in their structure. This stereogenic center may be present in a R and a S configuration, said R and S notation is used in correspondance with the rules described in Pure Appl. Chem., 1976, 45, 11–30.

Some of the compounds of formula (I) may also exist in their tautomeric forms. Such forms although not explicitly indicated in the above formula are intended to be included within the scope of the present invention. In particular, compounds of formula (I) wherein $R^3$ is hydrogen may exist in their corresponding tautomeric form.

Whenever used hereinafter, the term compounds of formula (I) is meant to include also the N-oxides, the pharmaceutically acceptable addition salts and all stereoisomeric forms.

A particular group of compounds comprises those compounds of formula (I) wherein $R^1$ represents hydrogen, C$_{1-6}$alkyl or aryl;

$R^2$ represents hydrogen; C$_{1-12}$alkyl; C$_{3-7}$cycloalkyl; C$_{2-8}$alkenyl; aryl; or C$_{1-12}$alkyl substituted with one or two substituents selected from C$_{3-7}$cycloalkyl, hydroxy, C$_{1-4}$alkyloxy, cyano, amino, mono- and di(C$_{1-4}$alkyl)amino, mono- and di(aryl)amino, arylC$_{1-4}$alkylamino, (C$_{1-4}$alkyl)(arylC$_{1-4}$alkyl)-amino, pyrrolidinyl, piperidinyl, piperazinyl, morpholinyl, perhydro-azepinyl, carboxyl, C$_{1-4}$alkyloxycarbonyl, aminocarbonyl, mono- and di(C$_{1-4}$alkyl) aminocarbonyl, aryl, aryloxy and arylthio;

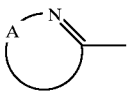

represents an unsaturated mono- or bicyclic heterocycle selected from the group consisting of 2-pyridinyl, 3-pyridazinyl, 2-pyrimidinyl, 4-pyrimidinyl, 2-pyrazinyl, 2-quinolinyl, 1-isoquinolinyl, 3-isoquinolinyl, 1-phtalazinyl, 3-cinnolinyl, 2-quinazolinyl, 4-quinazolinyl and 2-quinoxalinyl; each of said unsaturated mono- or bicyclic heterocycles may optionally be substituted with one, two or three substituents selected from hydroxy, halo, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl; or

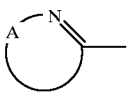

represents a radical of formula (a) or (b) wherein $R^4$ and $R^5$ each independently represent hydrogen, hydroxy, halo, nitro, amino, $C_{1-6}$alkyl, hydroxy-$C_{1-6}$alkyl, halo$C_{1-6}$alkyl, $C_{1-6}$alkyloxy, formyl, carboxyl, mono- or di($C_{1-6}$alkyl)-amino, $C_{1-6}$alkyloxycarbonyl or aryl.

A group of interesting compounds comprises those compounds of formula (I) wherein
$R^1$ represents hydrogen, hydroxy, $C_{1-6}$alkyl;
$R^2$ represents hydrogen; $C_{1-12}$alkyl; $C_{3-7}$cycloalkyl; pyrrolidinyl optionally substituted with $C_{1-4}$alkyl or $C_{1-4}$alkyloxycarbonyl; aryl or $C_{1-12}$alkyl substituted with one or two substituents selected from hydroxy, $C_{1-4}$alkyloxy, mono- and di($C_{1-4}$alkyl)amino, ($C_{1-4}$alkyl)(aryl$C_{1-4}$alkyl)amino, $C_{1-4}$alkyloxycarbonyl, morpholinyl, piperidinyl, piperazinyl optionally substituted with $C_{1-4}$alkyl, and aryloxy;
$R^3$ represents hydrogen and $C_{1-6}$alkyl;
Het represents imidazolyl optionally substituted with $C_{1-6}$alkyl; pyridinyl or triazolyl;

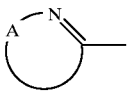

represents 2-pyridinyl optionally substituted with hydroxy$C_{1-6}$alkyl, formyl or $C_{1-6}$alkyloxycarbonyl; 2-quinoxalinyl; 1-isoquinolinyl; 2-quinolinyl; 3-pyridazinyl optionally substituted with $C_{1-6}$alkyl; purinyl; 2-pyrazinyl; 1-phtalazinyl; 4-quinazolinyl optionally substituted with aryl; 2-pyrimidinyl; 4-pyrimidinyl optionally substituted with $C_{1-6}$alkylthio; or

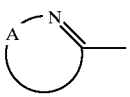

represents a radical of formula (a) or (b), wherein:
X represents NH, O or S;
$R^4$ and $R^5$ each independently represent hydrogen, hydroxy, nitro, cyano, amino, $C_{1-6}$alkyl or aryl;

—$R^6$—$R^7$— represents a bivalent radical of formula (b-1), (b-2) or (b-10), wherein each $R^9$ independently represents hydrogen, $C_{1-6}$alkyl, hydroxy, halo, amino, halo$C_{1-6}$alkyl or $C_{1-6}$alkyloxy.

Of special interest are those compounds of formula (I) wherein Het is optionally substituted imidazolyl or triazolyl, in particular, 1-imidazolyl optionally substituted with $C_{1-6}$alkyl or aryl; 2-imidazolyl optionally substituted with $C_{1-6}$alkyl; 5-imidazolyl optionally substituted with $C_{1-6}$alkyl; 1,3,4-triazol-1-yl and 1,2,4-triazol-1-yl.

Also of special interest are those compounds of formula (I) wherein

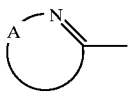

represents a radical of formula (b), particularly those wherein
X represents O or S; and
—$R^6$—$R^7$— represents a bivalent radical of formula (b-1).

Other compounds of special interest are those compounds of formula (I) wherein $R^2$ represents $C_{1-12}$alkyl; $C_{3-7}$cycloalkyl; aryl or $C_{1-12}$alkyl substituted with mono- or di($C_{1-4}$alkyl)amino, $C_{1-4}$alkyloxycarbonyl or aryloxy.

Particular compounds are those compounds of special interest wherein Het is 1-imidazolyl optionally substituted with $C_{1-6}$alkyl or aryl; 2-imidazolyl optionally substituted with $C_{1-6}$alkyl; 5-imidazolyl optionally substituted with $C_{1-6}$alkyl; 1,3,4-triazol-1-yl and 1,2,4-triazol-1-yl; $R^2$ represents $C_{1-12}$alkyl; $C_{3-7}$cycloalkyl; aryl or $C_{1-12}$alkyl substituted with mono- or di($C_{1-4}$alkyl)amino; and

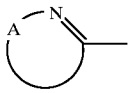

represents a radical of formula

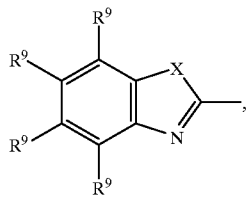

wherein X represents O or S.

Preferred compounds are those compounds of formula (I) wherein $R^1$ is hydrogen and $R^2$ is $C_{3-7}$cycloalkyl or $C_{1-6}$alkyl optionally substituted with di($C_{1-6}$alkyl)amino.

Most preferred are the compounds
N-[4-[2-ethyl-1-(1H-imidazol-1-yl)butyl]phenyl]-2-benzothiazolamine;
N-[4-[2-ethyl-1-(1H-1,2,4-triazol-1-yl)butyl]phenyl]-2-benzoxazolamine;
N-[4-[2-ethyl-1-(1H-1,2,4-triazol-1-yl)butyl]phenyl]-2-benzothiazolamine;
N-[4-[2-(dimethylamino)-1-(1H-imidazol-1-yl)propyl]phenyl]-2-benzothiazolamine;
N-[4-[2-(dimethylamino)-1-(1H-1,2,4-triazol-1-yl)propyl]phenyl]-2-benzothiazolamine;

N-[4-[2-ethyl-1-(1H-imidazol-1-yl)butyl]phenyl]-2-benzoxazolamine;
N-[4-[2-ethyl-1-(1H-imidazol-1-yl)butyl]phenyl]-6-methoxy-2-benzothiazolamine;
N-[4-[2-(dimethylamino)-1-(1 H-imidazol-1-yl)-2-methylpropyl]phenyl]-2-benzothiazolamine;
N-[4-[2-(dimethylamino)-2-methyl-1-(1H-1,2,4-triazol-1-yl)propyl]phenyl]-2-benzothiazolamine;
N-[4-[cyclohexyl(1H-imidazol-1-yl)methyl]phenyl]-2-benzothiazolamine;
N-[4-[cyclohexyl(1H-1,2,4-triazol-1-yl)methyl]phenyl]-2-benzothiazolamine; the
N-oxides, the stereochemically isomeric forms and the pharmaceutically acceptable addition salts thereof.

Whenever used hereinafter, $R^1$ to $R^3$, Het, aryl and

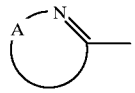

are defined as under formula (I) unless otherwise indicated.

In general, the compounds of formula (I) can be prepared by reacting an intermediate of formula (II) wherein $W^1$ is an appropriate leaving group such as, for example, a halogen, hydroxy or an alkylsulfonyloxy group, with an intermediate of formula (III) or a functional derivative thereof. For instance, a functional derivative of imidazole may be 1,1'-carbonyldiimidazole.

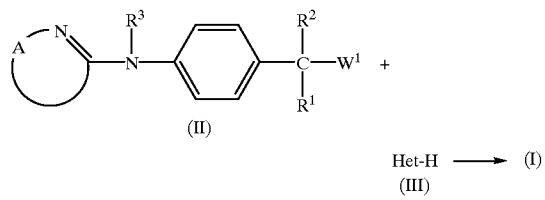

Said reaction may be performed in a reaction-inert solvent such as, for example, acetonitrile or tetrahydrofuran, in the presence of a suitable base such as, for example, potassium carbonate. In case $W^1$ is an hydroxy group, it may be convenient to perform the above reaction in the presence of triphenylphosphine and diethyl azodicarboxylate or a functional derivative of any of said reagents.

In this and the following preparations, the reaction products may be isolated from the reaction medium and, if necessary, further purified according to methodologies generally known in the art such as, for example, extraction, crystallization, distillation, trituration and chromatography.

Alternatively, compounds of formula (I) may be prepared by N-alkylation of an intermediate of formula (IV) with an intermediate of formula (V) wherein $W^2$ is an appropriate leaving group such as, for example, a phenoxy group, in a reaction-inert solvent such as, for example, N,N-dimethylformamide.

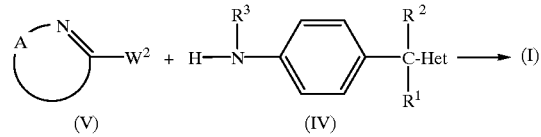

Compounds of formula (I) wherein

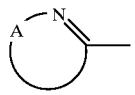

is a radical of formula (a) wherein X represents S, said compounds being represented by formula (I-a-1), can be prepared by reacting an intermediate of formula (VI) with an intermediate of formula (VII) wherein $W^3$ is an appropriate leaving group and in a reaction-inert solvent such as, for example, tetrahydrofuran.

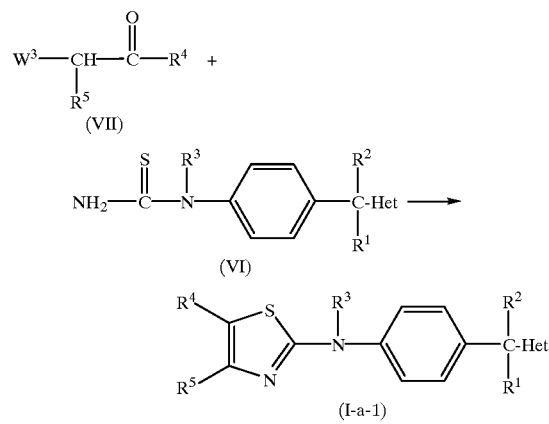

Suitably, intermediates of formula (VII) may be replaced by a functional derivative thereof such as, for example, the ketalized derivative thereof. In case the carbonyl group in the intermediates of formula (VII) is ketalized, the reaction is suitably performed in the presence of an acid such as, for example, hydrochloric acid.

The compounds of formula (I) wherein $R^3$ is hydrogen and

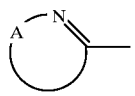

is a radical of formula (b) wherein X represents S, said compounds being represented by formula (I-b-1), can be prepared by reacting an intermediate of formula (VIII) with an intermediate of formula (IX-1) in a reaction-inert solvent such as, for example, tetrahydrofuran or 1-methyl-2-pyrrolidinone.

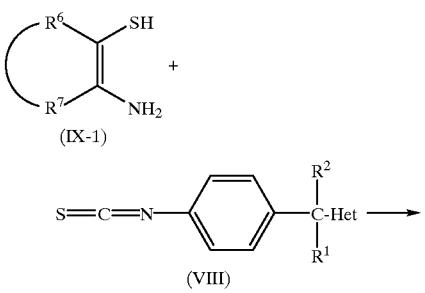

9

-continued

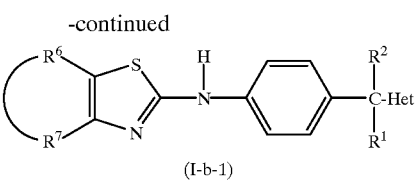

(I-b-1)

In the above reaction, intermediate (IX-1) may be replaced by an intermediate of formula (IX-2) thus forming a compound of formula (I-a-1) wherein $R^3$ is hydrogen and $R^4$ is amino, said compounds being represented by formula (I-a-2).

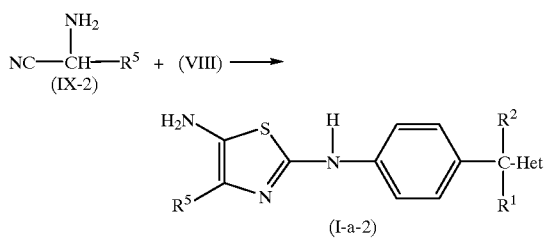

As an alternative to intermediate (VIII), the reaction may also be performed using an intermediate of formula (X). Said reaction is then performed in a reaction-inert solvent such as, for example, dimethylsulfoxide, and in the presence of a suitable base such as, for example, sodium hydroxide.

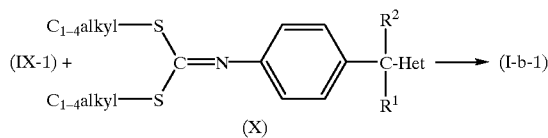

Compounds of formula (I) wherein $R^1$ is hydroxy may be prepared by reacting an intermediate corresponding to a compound of formula (I) wherein $R^1$ and $R^2$ together with the carbon atom to which they are attached form a carbonyl group, with Het-H (III) or a functional derivative thereof, in the presence of an appropriate reagent such as, for example, n-butyllithium, in a reaction-inert solvent such as tetrahydrofuran, and optionally in the presence of chlorotriethylsilane.

Compounds of formula (I) wherein $R^2$ is $C_{1-4}$alkyloxy$C_{1-12}$alkyl can be prepared by reacting an intermediate corresponding to a compound of formula (I) wherein $R^2$ is L-$C_{1-12}$alkyl wherein L is an appropriate leaving group such as, for example, a alkylsulfonyloxy group, with $C_{1-4}$alkylO$^-$ M$^+$ wherein M$^+$ is a suitable metal ion such as, for example Na$^+$, in a suitable solvent such as methanol.

Compounds of formula (I) wherein $R^2$ is optionally substituted $C_{1-12}$alkyl can be prepared by reducing an intermediate corresponding to a compound of formula (I) wherein said $R^2$ is connected to the carbon atom bearing the $R^2$ substituent by a double bond using a suitable reducing agent such as, for example, sodiumborohydride, in a suitable solvent such as methanol.

The compounds of formula (I) can also be converted into each other following art-known procedures of functional group transformation.

For example, compounds of formula (I) wherein $R^3$ is hydrogen may be converted to compounds of formula (I) wherein $R^3$ is other than hydrogen.

Also, compounds of formula (I) containing a $C_{1-6}$alkyloxycarbonyl substituent, may be transformed to

10 compounds of formula (I) wherein said substituent is reduced to hydroxymethyl; and if desired, said hydroxymethyl substituent may be further transformed to a formyl group.

Compounds of formula (I-a-2) wherein $R^5$ is cyano can be further reacted with HN=CH—NH$_2$ or a functional derivative thereof, thus forming the corresponding compound of formula (I-b-1) wherein —$R^6$—$R^7$— is —N=CH—N=C(NH$_2$)—.

Compounds of formula (I) wherein $R^1$ is hydroxy can be converted to compounds of formula (I) wherein R' is hydrogen using a suitable reagent such as stannous chloride.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures.

In particular, intermediates of formula (II) wherein $R^1$ and $R^3$ are hydrogen, $W^1$ is hydroxy and

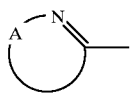

is a radical of formula (b), said intermediates being represented by formula (II-b-1), may be prepared by reacting an intermediate of formula (IX) with an intermediate of formula (XI-1) or (XI-2), and subsequently reducing the thus formed intermediate.

Intermediates of formula (IV) may be prepared by reacting an intermediate of formula (XII), wherein P is a protective group such as, for example, $C_{1-4}$alkylcarbonyl, benzoyl or $C_{1-4}$alkyloxycarbonyl, with an intermediate of formula (III), and by subsequently reacting the thus formed amide derivative with an acid such as, for example, hydrochloric acid. The preparation of the intermediate amide derivative may be performed using the same procedure as the one used for the preparation of compounds of formula (I) starting form an intermediate of formula (II) and (II).

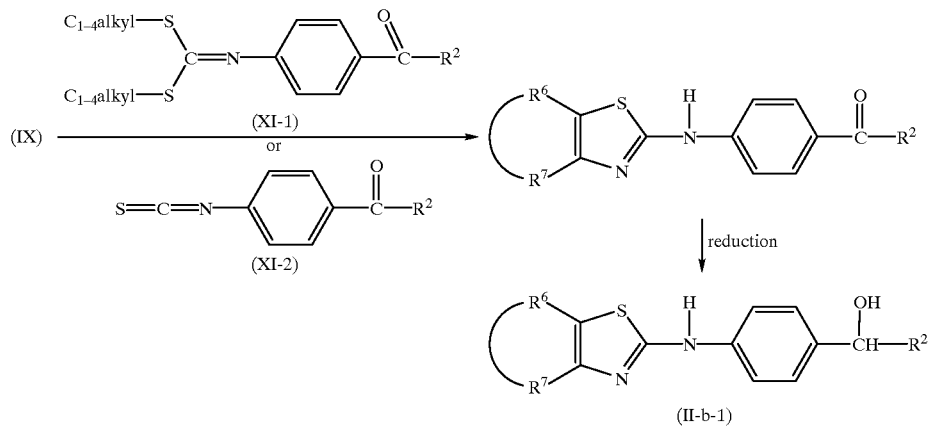

The first reaction involves the same procedure as the one used hereinabove for the preparation of compounds of formula (I-b-1) starting from an intermediate of formula (IX) and an intermediate of formula (VIII) or (X). The reduction may be performed in the presence of a suitable reducing agent in an appropriate reaction-inert solvent such as, for example, sodiumborohydride in methanol or lithiumaluminiumhydride in tetrahydrofuran and water.

In some instances, it may be convenient to replace the hydroxy group in intermediates of formula (II-b-1) by another leaving group such as, for example, a halogen or a sulfonyl derivative, e.g. a p-toluenesulfonyloxy group or a alkylsulfonyloxy group, thus forming intermediates of formula (II-b-2) or (II-b-3). Said reaction can be performed in a reaction-inert solvent, such as, for example, chloroform, and in the presence of a suitable reagent such as, for example, thionylchloride or methylsulfonyl chloride.

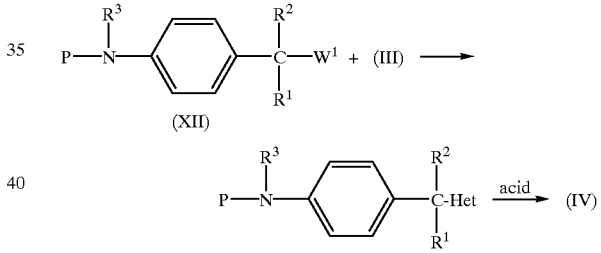

Intermediates of formula (VI) can be prepared by further reacting an intermediate of formula (IV) with a combination of two suitable reagents such as, for example, $NH_4SCN$ in combination with benzoylchloride or a functional derivative of any one of said reagents, in a reaction-inert solvent such

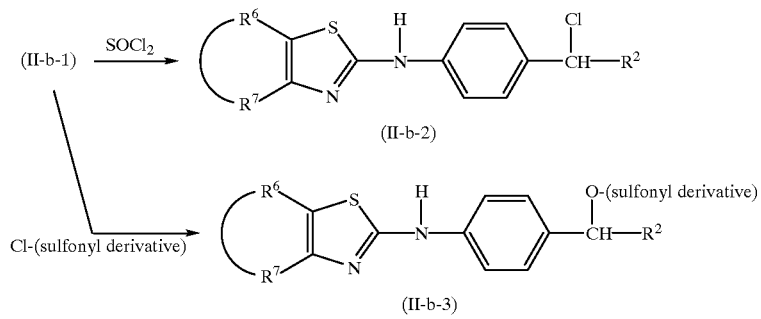

as, for example, 2-propanone. The thus formed intermediate may be deprotected using a suitable base such as, for example, sodium hydroxide.

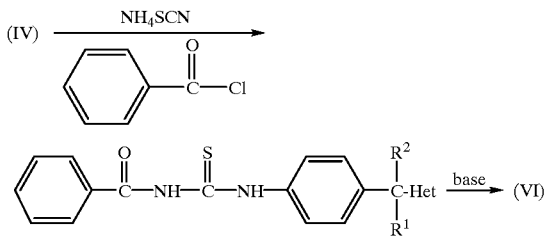

Intermediates of formula (IV) wherein $R^3$ is hydrogen, said intermediates being represented by formula (IV-a), may also be reacted with an appropriate reagent such as $CSCl_2$ or a functional derivative thereof, in a reaction inert solvent and in the presence of a suitable base such as, for example, sodium hydroxide, thus forming intermediates of formula (VIII).

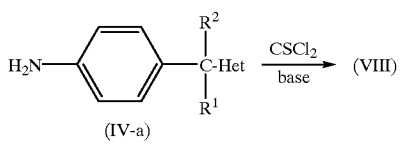

Also, intermediates of formula (IV-a) may further be used in the preparation of intermediates of formula (X). Said preparation involves the reaction of an intermediate of (IV-a) with $CS_2$ and $CH_3$-I or a functional derivatives of any one of said reagents, in a reaction-inert solvent and in the presence of a base such as, for example, sodium hydroxide.

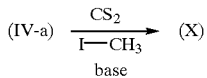

The compounds of formula (I) suppress the plasma elimination of retinoids, such as all-trans-retinoic acid, 13-cis retinoic acid and their derivatives, resulting in more sustained plasma and tissue concentrations of retinoic acid and improved control of the differentiation and growth of various cell types. This action of the present compounds is also called retinoic mimetic activity because administering a compound of formula (I) causes the same effect as if retinoids were administered. As such, the present compounds can be used to control the rate of growth and differentiation of normal, preneoplastic and neoplastic cells, whether they are epithelial or mesenchymal; whether they are of ectodermal, endodermal or mesodermal origin.

The property to delay the metabolism of retinoic acid can be evidenced in various in vitro and in vivo experiments. A particular in vitro procedure is described in example C.1 and tests the inhibitory activity of the compounds of formula (I) on the metabolism of retinoic acid in human breast cancer cells. The compounds of the present invention were also effective in suppressing induced vaginal keratinization effects in ovariectomized rats as is described in example C.2.

In addition, the compounds of formula (I) show little or no endocrinological side-effects and they have good oral availability.

In view of the above described pharmacological properties, in particular their retinoic mimetic activity, the present compounds are useful in the treatment and/or the prevention of disorders characterized by abnormal proliferation and/or abnormal differentiation of cells, in particular of cells of which the growth and differentiation is sensitive to the actions of retinoids. Such disorders are situated in the field of oncology, for example, head- and neck cancer, lung cancer, breast cancer, uterine cervix cancer, gastrointestinal tract cancer, skin cancer, bladder cancer and prostate cancer and similar disorders; and in the field of dermatology, for example, keratinization disorders such as rosacea, acne, psoriasis, severe psoriasis, lamellar ichthyosis, plantar warts, callosities, acanthosis nigricans, lichen planus, molluscum, melasma, corneal epithelial abrasion, geographic tongue, Fox-Fordyce disease, cutaneous metastatic melanoma and keloids, epidermolytic hyperkeratosis, Darier's disease, pityriasis rubra pilaris, congenital ichthyosiform erythroderma, hyperkeratosis palmaris et plantaris, melasma, hyperpigmentation and similar disorders.

Further, the compounds of formula (I) are useful in suppressing the metabolism of exogenously administered and of endogenously formed 1α,25-dihydroxy-vitamin $D_3$ (calcitriol). The inhibitory activity of the compounds of formula (I) on the metabolic degradation of calcitriol may be evidenced by measuring the impact of said compounds on the calcitriol degradation in human foreskin keratinocytes, pig kidney cells and human hepatoma cells. In view of their inhibitory effect on the calcitriol metabolism, the compounds of formula (I) can be used in the treatment of vitamin D deficiency states. The "classic" application of vitamin D compounds lies in the field of metabolic bone disorders. Calcitriol has also been described to influence the effects and/or production of interleukins. Further, calcitriol is of use in the treatment of diseases characterized by abnormal cell proliferation and/or differentiation, in particular, keratinization disorders such as those described hereinabove (Bouillon et al., Endocrine Reviews, 1995, 16, 200–257).

In view of the above described uses of the compounds of formula (I), it follows that the present invention provides a method of treating warm-blooded animals suffering from diseases which are characterized by an abnormal proliferation and/or abnormal differentiation of normal, preneoplastic or neoplastic cells, whether they are epithelial or mesenchymal; whether they are of ectodermal, endodermal or mesodermal origin. Said method comprises the systemic or topical administration of a retinoic mimetic amount of a compound of formula (I) effective in treating the above described disorders, in particular keratinization disorders such as psoriasis, optionally in the presence of an effective amount of a retinoic acid, a derivative or a stereochemically isomeric form thereof. The present invention further concerns a method of treating patients suffering from a pathological condition which may be beneficially influenced by the administration of calcitriol or a prodrug thereof, in particular keratinization disorders such as psoriasis, said method consisting of administering to a patient (a) an effective amount of calcitriol or a prodrug thereof and (b) an effective amount of a compound of formula (I).

Thus, the present invention also relates to compounds of formula (I) as defined hereinabove for use as a medicine, in particular, for use in the manufacture of a medicament for the treatment of keratinization disorders such as psoriasis. The present invention further relates to compounds of formula (I) as defined hereinabove in combination with a retinoic acid, a derivative or a stereochemically isomeric form thereof, or in combination with calcitriol or a prodrug thereof, for use as a medicine.

For ease of administration, the subject compounds may be formulated into various pharmaceutical forms. As appropriate compositions there may be cited all compositions usually employed for systemically or topically administering drugs. To prepare the pharmaceutical compositions of this invention, a retinoic mimetic effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment. Addition salts of compounds of formula (I) due to their increased water solubility over the corresponding base form, are obviously more suitable in the preparation of aqueous compositions.

As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular compositions, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (included scored or coated tablets), capsules, pills, powder packets, wafers, injectable solutions or suspensions, teaspoonfuls, tablespoonfuls and the like, and segregated multiples thereof.

Other such compositons are preparations of the cosmetic type, such as toilet waters, packs, lotions, skin milks or milky lotions. Said preparations contain, besides the active ingredient, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflamatory agents, antibacterials, antifungals, disinfectants, vitamins, sunscreens, antibiotics, or other anti-acne agents.

The present invention also provides particular pharmaceutical or cosmetical compositions which comprise an inert carrier, an effective amount of a compound of formula (I) and an effective amount of a retinoic acid, a derivative thereof or a stereochemically isomeric form thereof. Said retinoic acid containing compositions are particularly useful for treating acne or for retarding the effects of aging of the skin and generally improve the quality of the skin, particularly human facial skin. Further, the invention also relates to particular pharmaceutical or cosmetical compositions which comprise an inert carrier, an effective amount of a compound of formula (I) and an effective amount of calcitriol or a prodrug thereof. The latter compositions are particularly useful in treating keratinization disorders.

The invention also relates to a product containing retinoic acid or a derivative thereof and a compound of formula (I) as a combined preparation for simultaneous, separate or sequential use in dermatological or oncological disorders. The invention also relates to a product containing calcitriol or a prodrug thereof and a compound of formula (I) as a combined preparation for simultaneous, separate or sequential use in disorders beneficially affected by calcitriol. Such products may comprise, for example, a kit comprising a container with a suitable composition containing a compound of formula (I) and another container with a composition containing calcitriol or a retinoid Such a product may have the advantage that a physician can select on the basis of the diagnosis of the patient to be treated the appropriate amounts of each component and the sequence and timing of the administration thereof.

Those of skill in the treatment of the disorders described hereinabove could determine the effective therapeutic daily amount from the test results presented in the experimental part. An effective therapeutic daily amount would be from about 0.01 mg/kg to about 40 mg/kg body weight, more preferably from about 0.1 mg/kg to about 10 mg/kg body weight. It may be appropriate to administer the therapeutically effective dose once daily or as two, three, four or more sub-doses at appropriate intervals throughout the day. Said sub-doses may be formulated as unit dosage forms, for example, containing 0.1 mg to 500 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.

The following examples are intended to illustrate and not to limit the scope of the present invention.

Experimental part

Of some compounds of formula (I) the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. Said "A" and "B" forms of those compounds of formula (I) wherein two stereogenic carbon atoms are present were separated in their pure steroechemically isomeric forms and designated as "A1" and "A2", and "B1" and "B2", without further reference to the actual stereochemical configuration.

As used hereinafter, "THF" is defined as tetrahydrofuran, "EtOAc" is defined as ethylacetate, "DIPE" is defined as diisopropyl ether and "RT" is defined as room temperature.

A) Preparation of the intermediate compounds

EXAMPLE A-1 a) Benzoyl chloride (0.067 mol) was added to a solution of aminothiocyanate (5.09 g) in 2 propanone (150 ml) and the mixture was stirred and refluxed for 20 minutes. A solution of 4-[1-(1H-imidazol-1-yl)-2-methylpropyl] benzenamine (0.0557 mol) in 2-propanone (150 ml) was added and the mixture was stirred and refluxed at 80° C. overnight. The mixture was cooled, filtered through celite and the filtrate was evaporated. The residue was taken up in $CH_2Cl_2$. The organic layer was dried, filtered off and the solvent evaporated. The residue was purified by column chromatography over silica gel (eluent: $CH_2Cl_2/CH_3OH/NH_4OH$ 98/2/0.1). The pure fractions were collected and the solvent evaporated, yielding 15.2 g (72%) of (±)-N-benzoyl-N'-[4-[1-(1H-imidazol-1-yl)-2-methylpropyl]phenyl] thiourea (interm. 1).

b) A mixture of intermediate (1) (0.0329 mol) in NaOH (300 ml; 3N) was stirred and refluxed for 2 hours. The mixture was cooled, poured into ice, neutralized with concentrated HCl and extracted with $CH_2Cl_2$. The organic layer was dried, filtered off and the solvent evaporated, yielding 7.91 g (88%) of N'-[4-[1-(1H-imidazol-1yl)-2-methylpropyl]phenyl]thiourea (interm. 2).

EXAMPLE A-2 a) Sec butyllithium (298 ml; 1.3 M) was added dropwise at −60° C. under $N_2$ flow to a solution of N-(4-bromophenyl) acetamide (0.1892 mol) in THF (400 ml) and the mixture was stirred at −70° C. for 2 hours. A solution of 1-cyano-1-methyl-N,N-dimethylethanamine (0.075 mol) in THF (60 ml) was added dropwise, the mixture was brought to RT and then stirred at RT for 12 hours. The mixture was poured into ice and extracted with EtOAc. The solvent was evaporated, the residue was taken up in HCl (3 N) and EtOAc, extracted with EtOAc, basified with $K_2CO_3$ (10%) and extracted with $CH_2Cl_2$. The organic layer was separated, dried, filtered and the solvent was evaporated. The residue was recrystallized from $(C_2H_5)_2O$ and DIPE. The precipitate was filtered off and dried, yielding 6.8 g (36%) of N-[4-[2-(dimethylamino)-2-methyl-1-oxopropyl]phenyl]acetamide (interm. 3).

b) A mixture of intermediate (3) (0.026 mol) in HCl (180 ml; 6 N) was stirred and heated at 100° C. for 2 hours. The mixture was poured into ice, washed with EtOAc, basified with $NH_4OH$ and extracted with EtOAc. The organic layer was separated, dried, filtered and the solvent was evaporated, yielding 5.1 g (94%) of 1-(4-aminophenyl)-2-(dimethylamino)-2-methyl-1-propanone (interm. 4).

c) Carbonothioic dichloride (2.45 ml) was added dropwise at 0° C. to a solution of intermediate (4) (0.0247 mol) in NaOH (10.7 ml; 3 N) and $CHCl_3$ (200 ml) and the mixture was stirred at 0° C. for 4 hours. The mixture was poured into $K_2CO_3$ (10%) and extracted with $CH_2Cl_2$. The organic layer was separated, dried, filtered and the solvent was evaporated, yielding 6.1 g (99%) of 2-(dimethylamino)-2-methyl-1-(4-isothiocyanatophenyl)-1-propanone (interm. 5).

d) A mixture of intermediate (5) (0.0247 mol) and 2-aminobenzenethiol (0.0298 mol) in THF (60 ml) was stirred and refluxed for 2 hours and then stirred further at RT for 72 hours. The mixture was poured into water and extracted with EtOAc. The organic layer was separated, dried, filtered and the solvent was evaporated. The residue was crystallized from $(C_2H_5)_2O$ and DIPE. The precipitate was filtered off and dried, yielding 5.57 g (67%) of 1-[4-(2-benzothiazolylamino)phenyl]-2-(dimethylamino)-2-methyl-1propanone (interm. 6).

e) $NaBH_4$ (3.72 g) was added portionwise at 10° C. to a solution of intermediate (6) (0.0164 mol) in methanol (60 ml) and the mixture was stirred at RT for 24 hours. The mixture was poured into water and ice and extracted with $CH_2Cl_2$. The organic layer was separated, dried, filtered and the solvent was evaporated, yielding 5.2 g (93%) of 1-[4-(2-benzothiazolylamino)phenyl]-2-(dimethylamino)-2-methyl-1-propanol (interm. 7).

EXAMPLE A-3 a) A solution of lithium tetrahydroaluminate (0.1107 mol) in THF (100 ml) was added dropwise at 0° C. under $N_2$ flow to a suspension of ethyl 4-(2-benzothiazolylamino)-benzoate (0.1107 mol) in water. The mixture was brought to RT and stirred for 30 minutes. The mixture was hydrolized by adding water (8 ml) dropwise and then $CH_2Cl_2$ (50 ml), and a little $CH_3OH$ was added. The precipitate was filtered and the solvent was evaporated. The residue was crystallized from 2-propanone and DIPE. The precipitate was filtered off and dried, yielding 8 g (86%) of 4-(2-benzothiazolylamino) benzenemethanol (interm. 8).

b) Thionyl chloride (10 ml) was added dropwise at 0° C. to a solution of intermediate (8) (0.039 mol) in $CH_2Cl_2$ (100 ml) and the mixture was stirred at 0° C. for 2 hours.

The solvent was evaporated, yielding 10.7 g of N-[4-(chloromethyl)phenyl]-2-benzothiazolamine (interm. 9).

EXAMPLE A-4 a) A mixture of intermediate (8) (0.0312 mol) and manganese dioxide (0.115 mol) in $CH_2Cl_2$ (200 ml) and N,N-dimethylformamide (10 ml) was stirred at to RT for 12 hours. Manganese dioxide (0.115 mol) was added again and the mixture was stirred at RT for 12 hours. The mixture was filtered through celite, washed with $CH_2Cl_2$ and the solvent was evaporated. Water (100 ml) was added, evaporated, filtered, crystallized, filtered and dried, yielding 7 g (89%) of 4-(2-benzothiazolylamino)benzaldehyde (interm. 10).

b) A solution of 1-bromo-3-fluorobenzene (0.213 mol) in THF (60 ml) was added dropwise at RT under $N_2$ flow to a suspension of magnesium (0.213 mol) in THF (60 ml) and the mixture was stirred for 30 minutes. The mixture was cooled to 0° C., a solution of intermediate (10) (0.071 mol) in THF (60 ml) was added dropwise and the mixture was stirred for 15 minutes. The mixture was poured into water and $NH_4Cl$ and extracted with EtOAc. The organic layer was separated, dried, filtered and the solvent was evaporated. The residue was purified by column chromatography over silica gel (eluent: $CH_2Cl_2/CH_3OH/NH_4OH$ 100/0/0 to 90/10/0.1). The pure fractions were collected and the solvent was evaporated, yielding 22.4 g (90%) of (±)-α-[4-(2-benzothiazolylamino)phenyl]-3-fluorobenzenemethanol (interm. 11).

c) n Butyllitium (0.1836 mol; 1.6 M) was added dropwise at −70° C. under $N_2$ flow to a solution of N-(1-methylethyl)-2-propanamine (0.1836 mol) in THF (60 ml). The mixture was stirred for 20 minutes, while the mixture was allowed to warm to −30° C. A solution of ethyl propanoate (0.1836 mol) in THF (100 ml) was added at −78° C. The mixture was allowed to warm to −30° C. and then cooled to −78° C. A solution of intermediate (10) (0.0875 mol) in THF (60 ml) was added dropwise. The mixture was stirred at −60° C. for 20 minutes, then poured out into water and $NH_4Cl$ and extracted with EtOAc. The organic layer was separated, dried, filtered and the solvent was evaporated. The residue was purified by column chromatography over silica gel (eluent: $CH_2Cl_2/CH_3OH/NH_4OH$ 97/3/0.5). The pure fractions were collected and the solvent was evaporated. The residue was crystallized from 2-propanone and diethyl ether. The precipitate was filtered off and dried, yielding 18 g of (±)-ethyl 4-(2-benzothiazolylamino)-β-hydroxy-α-methylbenzenepropanoate (interm. 12).

EXAMPLE A-5 a) A solution of 3-bromopentane (0.331 mol) in $(C_2H_5)_2O$ (200 ml) was added dropwise to a solution of magnesium turnings (0.331 mol) in $(C_2H_5)_2O$, the mixture was stirred at RT for 2 hours and then cooled to 0° C. A solution of N-(4-formylphenyl)acetamide (0.11 mol) in THF (400 ml) was added dropwise and the mixture was stirred for 10 minutes. The mixture was poured into aqueous $NH_4Cl$ and extracted with EtOAc. The organic layer was dried, filtered off and the solvent evaporated. The residue was purified by column chromatography over silica gel (eluent: $CH_2Cl_2/CH_3OH/NH_4OH$ 97/3/0.1). The pure fractions were collected and evaporated, yielding 13.5 g (52%) of (±)-N-[4-(2-ethyl-1-hydroxybutyl)phenyl]acetamide (interm. 13).

b) Methanesulfonyl chloride (0.114 mol) was added dropwise at 0° C. under $N_2$ to a solution of intermediate (13) (0.057 mol) and triethylamine (0.114 mol) in $CH_2Cl_2$ (250 ml) and the mixture was stirred at RT for 12 hours. The solvent was evaporated, yielding 17.86 g (100%) of (±)-4-(acetylamino)-α-(1-ethylpropyl) benzenemethanol methanesulfonate (ester) (interm. 14).

c) A mixture of intermediate (14) (0.187 mol), 1H-1,2,4-triazole (0.561 mol) and potassium carbonate (0.561 mol) in methanol (600 ml) was stirred and refluxed for 20 hours. The mixture was poured into water and extracted with $CH_2Cl_2$. The organic layer was washed with water, dried, filtered off and the solvent evaporated. The residue was purified by column chromatography over silica gel (eluent: $CH_2Cl_2/CH_3OH/NH_4OH$ 96/4/0.1). The pure fractions were collected and evaporated, yielding 22 g (±)-N-[4-[2-ethyl-1-(1H-1,2,4-triazol-1-yl)butyl]phenyl]acetamide (41%) (interm. 15).

d) A mixture of intermediate (15) (0.0073 mol) in HCl (10 ml; 3 N) was stirred at 60° C. for 12 hours. The mixture was poured out into ice water, basified with a concentrated NaOH solution and extracted with EtOAc. The organic layer was separated, dried, filtered and the solvent was evaporated. The residue was purified by column chromatography over silica gel (eluent: $CH_2Cl_2/CH_3OH/NH_4OH$ 98.5/1.5/0.1). The pure fractions were collected and the solvent was evaporated. The residue was crystallized from methylethylketon/DIPE. The precipitate was filtered off and dried, yielding 1.8 g (73%) of (±)-4-[2-ethyl-1-(1H-1,2,4-triazol-1-yl)butyl]-benzenamine (interm. 16). The product was separated by HLPC Chiralpack AS 20 μm (eluent: hexane/$C_2H_5OH$ 65/35). The pure fractions were collected, evaporated and dried, yielding 0.54 g of (A)-4-[2-ethyl-1-(1H-1,2,4-triazol-1-yl)butyl]benzenamine (interm. 17), and 0.588 g of (B)-4-[2-ethyl-1-(1H-1,2,4-triazol-1-yl)butyl]benzenamine (interm. 18).

e) A mixture of $CS_2$ (0.0819 mol) in NaOH (3.8 ml; 20 N) was added at RT to a mixture of intermediate (16) (0.063 mol) in dimethylsulfoxide (37 ml). The mixture was stirred for 1 hour and cooled to 0° C. Iodomethane (4.9 ml) was added. The mixture was stirred at RT for 3 hours and cooled to 0C. NaOH (3.8 ml; 20 N) and iodomethane (4.9 ml) were added. The mixture was stirred at RT overnight. EtOAc and water were added and the mixture was extracted with EtOAc. The organic layer was separated, washed with water, dried, filtered and the solvent was evaporated, yielding 25 g of (±)-N-[bis(methylthio)methyl]-4-[2-ethyl-1-(1H-1,2,4-triazol-1-yl)butyl]benzenamine (interm. 19a).

f) Carbonothioic dichloride (0.216 mol) was added dropwise at 0° C. to a solution of intermediate (16) (0.1665 mol) in sodium hydroxide (3N; 72.15 ml) and $CH_2Cl_2$ (400 ml). The mixture was allowed to warm to RT over a 2-hour period while stirring and then poured out into $K_2CO_3$ (10%; 200 ml). The mixture was stirred for 30 minutes and then decanted. The organic layer was dried, filtered and the solvent was evaporated, yielding 47.7 g (100%) of (±)-1-[2-ethyl-1-(4-isothiocyanatophenyl)butyl]-1H-1,2,4-triazole (interm. 19b).

(±)-1-[1-(4-isothiocyanatophenyl)-2-ethylbutyl]-1H-imidazole (interm. 19c) was prepared similarly.

EXAMPLE A-6 a) A mixture of 1-(4-aminophenyl)-2-methyl-1-propanone (0.0637 mol) and methyl 2-chloro-3-pyridinecarboxylate (0.0637 mol) in 2-methoxyethanol (200 ml) was stirred and refluxed for 90 hours. The mixture was taken up in water and EtOAc and extracted with EtOAc. The organic layer was separated, dried, filtered and the solvent was evaporated, yielding 22.6 g of methyl 2-[[4-(2-methyl-1-oxopropyl)phenyl]amino]-3-pyridinecarboxylate (interm. 20).

b) Sodium tetrahydroborate (0.0764 mol) was added portionwise at 0° C. to a mixture of intermediate (20) (0.0637 mol) in methanol (200 ml). The mixture was stirred for 2 hours. Water was added and the organic solvent was evaporated. The concentrate was taken up in $CH_2Cl_2$, dried, filtered and the solvent was evaporated, yielding 18.38 g of (±)-methyl 2-[[4-(1-hydroxy-2-methylpropyl)phenyl]amino]-3-pyridinecarboxylate (interm. 21).

EXAMPLE A-7 a) Aluminium(III)chloride (0.666 mol) was added portionwise at RT to a solution of N-phenyl-2-benzothiazolylamine (0.222 mol) and 1,2dichloro-1-propanone (0.233 mol) in 1,2-dichloroethane (500 ml) and the mixture was stirred and heated at 80° C. for 2 hours. The mixture was poured into ice and extracted with $CH_2Cl_2$. The organic layer was decanted, dried filtered and the solvent was evaporated, yielding 68 g of (±)-1-[4-(2-benzothiazolylamino)phenyl]-2-chloro-1-propanone (95.7%) (interm. 22).

b) A mixture of intermediate (22) (0.0423 mol), N-methylethanamine (0.084 mol) and potassium carbonate (0.127 mol) in methanol (150 ml) was stirred and refluxed for 90 minutes. The mixture was poured out into water, extracted with $CH_2Cl_2$ and decanted. The organic layer was dried, filtered and the solvent was evaporated. The residue was purified by column chromatography over silica gel (eluent: $CH_2Cl_2$/2-propanol/$NH_4OH$ 95/5/0.1 and 90/10/0.1). The pure fractions were collected and the solvent was evaporated, yielding 6.85 g (54%) of (±)-1-[4-(2-benzothiazolylamino)-phenyl]-2-(ethylmethylamino)-1-propanone (interm. 23).

In a similar way, (±)-1-[4-(2-benzothiazolylamino)phenyl]-2-(dimethylamino)-1-propanone was prepared (interm. 24).

c) Sodiumborohydride (0.0642 mol) was added portionwise at 0 to −5° C. to a solution of intermediate 24 (0.0584 mol) in methanol (250 ml) and the mixture was stirred for 3 hours. The mixture was poured into water and extracted with $CH_2Cl_2$. The organic layer was decanted, dried, filtered and the solvent was evaporated, yielding 45 g of (±)-4-(2-benzothiazolylamino)-α-[1-(dimethylamino)ethyl]benzenemethanol (interm. 25).

EXAMPLE A.8 a) The following reaction was performed under a $N_2$ atmosphere. A mixture of N-(4-bromophenyl)-2-benzothiazolamine (0.492 mol) in THF (2700 ml) was stirred at −70° C. Butyllithium (0.984 mol; 2.5 M in hexane) was added dropwise at −65° C. The mixture was stirred for one hour. A solution of 2-ethyl-butanal (0.492 mol) in THF (300 ml) was added dropwise at −75° C. The mixture was allowed to warm to RT overnight. A 10% aqueous $NH_4Cl$ solution (3000 ml) was added and the mixture was stirred for 15 minutes. The separated aqueous phase was extracted with EtOAc (1000 ml). The separated organic layer was dried, filtered and the solvent evaporated. The residue was crystallized from methyl isobutyl keton. The precipitate was filtered off and dried, yielding 109 g (68%) of (±)-4-(2-benzothiazolylamino)-α-(1-ethylpropyl)benzenemethanol (interm 28).

b) A mixture of intermediate 28 (0.156 mol) and triethylamine (0.312 mol) in $CH_2Cl_2$ (500 ml) was stiffed at or 0° C. under $N_2$ flow. A mixture of methylsulfonylchloride (0.314 mol) in $CH_2Cl_2$ (500 ml) was added dropwise. The mixture stirred at 0° C. for 3 hours. The solvent was evaporated, yielding (±)-4-(2-benzothiazolylamino)-α-(1-ethylpropyl)-benzenemethanol methanesulfonate (ester) (interm. 26).

c) Toluene (150 ml) was added to intermediate 28 (0.0582 mol). The heterogeneous mixture was stirred at RT. A solution of thionylchloride (0.0644 mol) in toluene (50 ml) was added dropwise. The reaction mixture was stirred for 2 hours at RT, then cooled to 0° C. The precipitate was filtered off and dried at RT. yielding 25 g (±)-N-[4-(1-chloro-2-ethylbutyl)phenyl]-2-benzothiazolamine monohydrochloride (interm. 29).

EXAMPLE A.9

A mixture of (±)-α-(1-ethylpropyl)-4-[[2-(methylthio)-4-pyrimidinylamino]benzenemethanol, prepared according to the procedure described in example A.2.e, (0.0227 mol) in methanol (144 ml) was hydrogenated at RT for 2 days with Raney nickel (7.2 g) as a catalyst. After uptake of hydrogen (1 equiv), the catalyst was filtered through celite, washed with methanol and the filtrate was evaporated. The residue was purified by column chromatography over silica gel (eluent: $CH_2Cl_2/CH_3OH$ 95/5). The desired fractions were collected and the solvent was evaporated. The residue was crystallized from diethyl ether. The precipitate was filtered off and dried, yielding 1.02 g (17%) of (±)-α-(1-ethylpropyl)-4-(4-pyrimidinylamino)benzenemethanol (interm. 27).

EXAMPLE A.10 a) Compound 130 (0.009 mol) was added at 0° C. to thionylchloride (40 ml). The mixture was stirred at 0° C. for 90 minutes. The solvent was evaporated, yielding 3.5 g N-[4-[2-(dimethylamino)-1-(1-methyl-1H-imidazol-5-yl)-1-propenyl]phenyl]-2-benzothiazolamine (interm. 56).

b) Using a similar reaction procedure as described in example B-12 hereinafter, N-[4-[2-ethyl-1-(1-methyl-1H-imidzole-2-yl)-1-butenyl]phenyl]-2-benzothiazol amine (interm. 57) was prepared.

The following intermediates, all being racemic mixtures except for intermediate No. 55 which contains no chiral carbon atom, were prepared according to any one of the procedures above:

TABLE 1

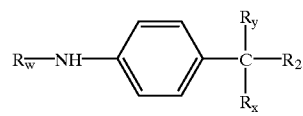

| Interm. No. | Ex. No. | $R_w$ | $R_x$ | $R_y$ | $R_z$ |
|---|---|---|---|---|---|
| 30 | A.1.b | C(=S)—$NH_2$ | H | 1H-imidazol-1-yl | $CH(C_2H_5)_2$ |
| 31 | A.3.b | 2-benzothiazolyl | H | Cl | $CH(CH_3)$—$N(CH_3)_2$ |
| 32 | A.3.b | 4-pyrimidinyl | H | Cl | $CH(C_2H_5)_2$ |
| 33 | A.3.b | 2-quinoxalinyl | H | Cl | $CH(C_2H_5)_2$ |
| 34 | A.4.b | 2-benzothiazolyl | $CH_3$ | OH | $CH(CH_3)$—$N(CH_3)_2$ |
| 35 | A.6.b | 2-quinolinyl | H | OH | $CH(C_2H_5)_2$ |
| 36 | A.6.b | 2-phenyl-4-quinazolinyl | H | OH | $CH(C_2H_5)_2$ |
| 37 | A.6.b | 2-quinoxalinyl | H | OH | $CH(C_2H_5)_2$ |
| 38 | A.6.b | 2-pyrimidinyl | H | OH | $CH(C_2H_5)_2$ |

TABLE 1-continued

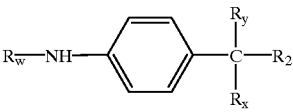

| Interm. No. | Ex. No. | $R_w$ | $R_x$ | $R_y$ | $R_z$ |
|---|---|---|---|---|---|
| 39 | A.7.c | 2-benzothiazolyl | H | OH | 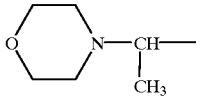 |
| 40 | A.7.c | 2-benzothiazolyl | H | OH | 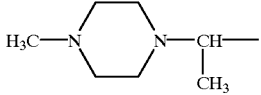 |
| 41 | A.7.c | 2-benzothiazolyl | H | OH | 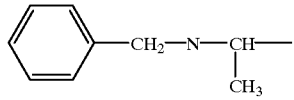 |
| 42 | A.8.c | 2-benzothiazolyl | H | O—SO$_2$—CH$_3$ | CH(CH$_3$)—N(C$_2$H$_5$)$_2$ |
| 43 | A.8.c | 2-benzothiazolyl | H | 1H-imidazol-1-yl | 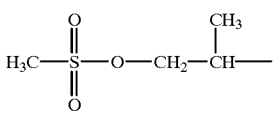 |
| 44 | A.8.c | 2-benzothiazolyl | H | O—SO$_2$—CH$_3$ | CH(CH$_3$)—N(CH$_3$)$_2$ |
| 45 | A.9 | 4-pyrimidinyl | H | OH | CH(C$_2$H$_5$)$_2$ |
| 46 | A.7.c | 2-benzothiazolyl | H | OH | 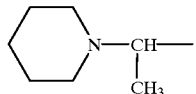 |
| 47 | A.6.b | 2-methylthio-4-pyrimidinyl | H | OH | CH(C$_2$H$_5$)$_2$ |
| 48 | A.8.c | 6-methyl-3-pyridazinyl | H | O—SO$_2$—CH$_3$ | CH(C$_2$H$_5$)$_2$ |
| 49 | A.6.b | 6-methyl-3-pyridazinyl | H | OH | CH(C$_2$H$_5$)$_2$ |
| 50 | A.6.b | 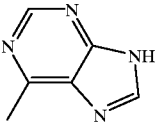 | H | OH | CH(C$_2$H$_5$)$_2$ |
| 51 | A.3.b | 2-pyrazinyl | H | Cl | CH(C$_2$H$_5$)$_2$ |
| 52 | A.6.b | 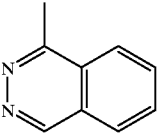 | H | OH | CH(C$_2$H$_5$)$_2$ |
| 53 | A.4.c | 2-benzothiazolyl | H | OH | 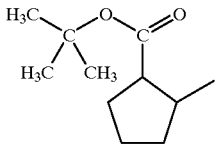 |

TABLE 1-continued

[Structure: $R_w$—NH—phenyl—C($R_y$)($R_x$)—$R_z$]

| Interm. No. | Ex. No. | $R_w$ | $R_x$ | $R_y$ | $R_z$ |
|---|---|---|---|---|---|
| 54 | A.3b | 1-methylphthalazinyl | H | Cl | $CH(C_2H_5)_2$ |
| 55 | A.6.a | 2-benzothiazolyl | | =O* | $CH(C_2H_5)_2$ |

*$R_x$ and $R_y$ are taken together

B) Preparation of the final compounds

EXAMPLE B-1

A mixture of intermediate (9) (0.0125 mol), 1H-imidazole (0.0584 mol) and potassium carbonate (0.0586 mol) in methanol (300 ml) was stirred and refluxed for 12 hours. The solvent was evaporated and the residue was taken up in water and $CH_2Cl_2$. The organic layer was separated, dried, filtered and the solvent was evaporated. The residue was purified by column chromatography over silica gel (eluent: $CH_2Cl_2/CH_3OH/NH_4OH$ 96.5/3.5/0.2). The pure fractions were collected and the solvent was evaporated. The residue was crystallized from 2-propanone and DIPE. The precipitate was filtered off and dried, yielding 1.65 g (28%) of N-[4-(1H-imidazol-1-ylmethyl)-phenyl]-2-benzothiazolamine (comp. 24).

EXAMPLE B-2

Triphenylphosphine (4.8 g) and 1H-1,2,4-triazole (0.018 mol) were added under $N_2$ flow at 5° C. to a solution of intermediate (7) (0.00732 mol) in THF. Then a solution of azodicarboxylate (2.88 ml) in THF was added, the mixture was brought to RT and then stirred for overnight. Water was added, the solvent was evaporated, acidified with HCl (3 N) and the layers were separated. The aqueous layer was washed with EtOAc, basified with $NH_4OH$ and extracted with EtOAc. The organic layer was separated, dried, filtered and the solvent was evaporated. The residue was purified by column chromatography over silica gel (eluent : $CH_2Cl_2/CH_3OH/NH_4OH$ 96/4/0.5). The pure fractions were collected and the solvent was evaporated. The residue was recrystallized from $(C_2H_5)_2O$. The precipitate was filtered off and dried, yielding 1 g (49%) (±)-N-[4-[2-(dimethylamino)-2-methyl-1-(1H-1,2,4-triazol-1-yl)propyl]-phenyl]-2-benzothiazolamine (comp. 38).

EXAMPLE B-3 a) A mixture of intermediate (19b) (0.1665 mol) and 2-aminobenzenethiol (0.2 mol) in THF (500 ml) was stirred and refluxed overnight. The mixture was cooled, poured out into water, extracted with $CH_2Cl_2$ and decanted. The organic layer was dried, filtered and the solvent was evaporated. The residue was purified by column chromatography over silica gel (eluent: $CH_2Cl_2/CH_3OH/NH_4OH$ 97.5/2.5/0.1. The pure fractions were collected and the solvent was evaporated. The residue was crystallized from 2-butanone/diethyl ether. The precipitate was filtered off and dried, yielding 31.2 g (49.6%) of (±)-N-[4-[2-ethyl-1-(1H-1,2,4-triazol-1-yl)butyl]phenyl]-2-benzothiazolamine (comp. 25).

b) Compound (25) (0.0265 mol) was separated and purified by chiral column chromatography over stationary phase Chiralcel OJ (eluent: hexane/ethanol 50/50). Two desired fraction groups were collected and their solvent was evaporated. Fraction 1 was crystallized from 2-propanol. The precipitate was filtered off, washed with 2-propanol, then dried, yielding 2 g (20%) of (A)-N-[4-[2-ethyl-1(1H-1,2,4-triazol-1-yl)butyl]-phenyl]-2-benzothiazolamine (comp. 33).

Fraction 2 was crystallized from 2-propanol. The precipitate was filtered off and dried, yielding 1.9 g (19%) of (B)-N-[4-[2-ethyl-1-(1H-1,2,4-triazol-1-yl)butyl]phenyl]-2-benzothiazolamine (comp. 34). The corresponding filtrate of the crystallized fraction 2 was evaporated. Part of the residue was dissolved in 2-propanol and converted into the (E)-2-butenedioic acid salt (2:3). The precipitate was filtered off and dried, yielding 3 g of (B)-N-[4-[2-ethyl-1-(1H-1,2,4-triazol-1-yl)butyl]-phenyl]-2-benzothiazolamine (E)-2-butenedioate(2:3) (comp. 35).

c) 2-methyl-2-propanol, potassium salt (0.0127 mol) was added portionwise at 0° C. to a solution of compound (25) (0.0106 mol) in THF (30 ml) and the mixture was stirred at 0° C. for 10 minutes. A solution of iodomethane (0.0127 mol) in THF (10 ml) was added slowly and the mixture was stirred at RT for 12 hours. The mixture was poured into water and extracted with $CH_2Cl_2$. The organic layer was separated, dried, filtered and the solvent was evaporated. The residue was purified by column chromatography over silica gel (eluent: $CH_2Cl_2/CH_3OH/NH_4OH$ 98.5/1.5/0.1). The pure fractions were collected and the solvent was evaporated. The residue was crystallized from 2-butanone and DIPE. The precipitate was filtered off and dried. The residue was recrystallized from 2-butanone. The precipitate was filtered off and dried, yielding 1.5 g (36%) of (±)-N-[4-[2-ethyl-1-(1H-1,2,4-triazol-1-yl)butyl]phenyl]-N-methyl-2-benzothiazolamine (comp. 32).

EXAMPLE B-4 a) NaOH (6.35 ml; 20 N) was added at RT to a solution of 2-aminobenzenethiol (0.0637 mol) in dimethylsulfoxide (115 ml). The mixture was stirred at RT for 30 minutes. (±)-β-[4-[[bis(methylthio)methylene]amino]phenyl]-N,N, α-trimethyl-1H-imidazol-1-ethanamine (0.0637 mol), prepared according to intermediate (19a), was added. The mixture was stirred at 110° C. overnight, then poured out on ice, extracted with EtOAc and washed with HCl (3 N). The aqueous layer was basified with a concentrated NH$_4$OH solution and extracted with EtOAc. The organic layer was separated, dried, filtered and the solvent was evaporated. The residue was separated by column chromatography over silica gel (eluent: CH$_2$Cl$_2$/CH$_3$OH/NH$_4$OH 97/3/0.1 and 90/10/0.1). Two pure fractions (F1 and F2) were collected and their solvents were evaporated. F1 was crystallized from 2-propanone. The precipitate was filtered off and dried. The residue was taken up in K$_2$CO$_3$ (10%), filtered and the solvent was evaporated, yielding 1.12 g (5%) (±)-(A)-N-[4-[2-(dimethylamino)-1-(1H-imidazol-1-yl)propyl]phenyl]-2-benzothiazolamine (comp. 1). F2 was crystallized from 2-propanone. The precipitate was filtered off and dried. The residue was recrystallized from 2-propanone. The precipitate was filtered off and dried, yielding 0.9 g (4%) of (±)-(B)-N-[4-[2-dimethylamino)-1-(1 H-imidazol-1-yl) propyl]phenyl]-2-benzothiazolamine (comp. 2).

b) Compound (2) (0.021 mol) was separated by HPLC Chiralpack AS (eluent : hexane/C$_2$H$_5$OH 87/13 to 70/30). The pure fractions were collected and the solvent was evaporated. Fraction 1 was taken up in DIPE. The precipitate was filtered off and dried, yielding 2.54 g (B1)-N-[4-[2-(dimethylamino)-1-(1H-imidazol-1yl)propyl]-phenyl]-2-benzothiazolamine (32%) (comp. 3). Fraction 2 was taken up in diethylether. The precipitate was filtered off and dried, yielding 2.41 g (B2)-N-[4-[2-(dimethylamino) -1-(1H-imidazol-1-yl)propyl]phenyl]-2-benzothiazolamine (30.3%) (comp. 4).

EXAMPLE B-5 a) 1,1'-carbonylbis-1H-imidazole (0.122 mol) was added at 60° C. to a mixture of intermediate (21) (0.0612 mol) in THF (250 ml). The mixture was stirred overnight, poured out into water and extracted with EtOAc. The organic layer was separated, dried, filtered and the solvent was evaporated. The residue was purified by column chromatography over silica gel (eluent: CH$_2$Cl$_2$/CH$_3$OH/NH$_4$OH 99.25/0.75/0.1). The pure fractions were collected and the solvent was evaporated. Part of the residue (2 g) was crystallized from CH$_3$OH/2-propanone/DIPE. The precipitate was filtered off and dried, yielding 1.6 g (40%) of (±)-methyl 2-[[4-[1-(1H-imidazol-1-yl)-2-methylpropyl]phenyl]amino]-3-pyridinecarboxylate (comp. 52).

b) Lithiumaluminium hydride (0.0242 mol) was added portionwise at 0° C. under N$_2$ flow to THF (100 ml). A solution of compound (52) (0.022 mol) in THF (200 ml) was added dropwise at 0° C. The mixture was stirred for 7 hours, then cooled to 0° C., hydrolized with EtOAc and water and filtered over celite. The solvent was evaporated, yielding 6.5 g of (93%) (±)-2-[[4-[1-(1H-imidazol-1-yl)-2-methylpropyl]phenyl]-amino]-3-pyridinemethanol (comp. 54).

c) A mixture of compound (54) (0.02 mol) and manganese (IV)oxide (65 g) in CH$_2$Cl$_2$ (200 ml) was stirred at RT for 16 hours. The mixture was filtered over celite and the solvent was evaporated, yielding 5.2 g (81%) of (+)-2-[[4-[1-(1H-imidazol-1-yl)-2-methylpropyl]phenyl]amino]-3-pyridinecarboxaldehyde (comp. 55).

EXAMPLE B-6

2-phenoxy-1,3-benzoxazole (0.0123 mol) was added to a solution of intermediate (16) (0.0123 mol) in N,N-dimethylformamide (20 ml). The mixture was stirred and refluxed at RT for 12 hours and then overnight. EtOAc was added. The mixture was poured out into water and extracted with EtOAc. The organic layer was separated, washed with water, dried, filtered and the solvent was evaporated. The residue was purified by column chromatography over silica gel (eluent: cyclohexane/2-propanol/NH$_4$OH 90/10/0.5). The pure fractions were collected and the solvent was evaporated. The residue was crystallized from DIPE. The precipitate was filtered off and dried, yielding 2.04 g (49.5%) of N-[4-[2-ethyl-1-(1H-1,2,4-triazol-1-yl)butyl] phenyl]-2-benzoxazolamine (comp. 56).

EXAMPLE B-7

A mixture of intermediate (2) (0.0123 mol) in 1-chloro-2-propanone (1.08 ml) and ethanol (20 ml) was stirred and refluxed for 3 hours. The mixture was cooled and the solvent evaporated. The residue was taken up in CH$_2$Cl$_2$ and washed with K$_2$CO$_3$ (10%) and water. The organic layer was dried, filtered off and evaporated. The residue was crystallized from 2-propanone and (C$_2$H$_5$)$_2$O, yielding 3.08 g (80%) of (±)-N-[4-[1-(1H-imidazol-1-yl)-2-methylpropyl]phenyl]4-methyl-2-thiazolamine (comp. 50).

EXAMPLE B-8

A mixture of intermediate (2) (0.0269 mol) and 2-bromo-1,1-diethoxyethane (0.035 mol) in HCl (11.8 ml; 3 N) and ethanol (200 ml) was stirred and refluxed for 3 hours. The mixture was cooled and evaporated. The residue was taken up in CH$_2$Cl$_2$ and K$_2$CO$_3$ (10%) and extracted with CH$_2$Cl$_2$. The organic layer was washed with water and K$_2$CO$_3$ (10%), dried, filtered off and the solvent evaporated. The residue was purified by column chromatography over silica gel (eluent: CH$_2$Cl$_2$/CH$_3$OH/NH$_4$OH 96/4/0.2). The pure fractions were collected and evaporated. The residue was crystallized from 2-propanone and DIPE, yielding 0.9 g (11%) of (±)-N-[4-[1-(1H-imidazol-1-yl)-2-methylpropyl]phenyl]-2-thiazolamine (comp. 51).

EXAMPLE B-9

Methanimidamide acetate (0.0309 mol) was added to a solution of compound 113 (0.0155 mol) in 1-methyl-2-pyrrolidinone (35 ml). The mixture was stirred and refluxed for 2 hours, then cooled, poured out into water and extracted with CH$_2$Cl$_2$. The organic layer was separated, dried, filtered and the solvent was evaporated. The residue (28.4 g) was purified by column chromatography over silica gel (eluent: CH$_2$Cl$_2$/CH$_3$OH/NH$_4$OH 96/4/0.1). The pure fractions were collected and the solvent was evaporated. The residue was crystallized from CH$_3$OH. The precipitate was filtered off, washed with diethyl ether and dried, yielding 1.66 g of (±)-N$^2$-[4-[2-ethyl-1-(1H-1,2,4-triazol-1-yl)butyl]-phenyl] thiazolo[5,4-d]pyrimidine-2,7-diamine (comp. 117).

EXAMPLE B-10

A mixture of intermediate 43 (0.0089 mol) and CH$_3$ONa 30% in CH$_3$OH (0.0445 mol) in CH$_3$OH (81 ml) was stirred and refluxed for 15 hours. The mixture was cooled, poured out into water, saturated with NaCl and extracted with CH$_2$Cl$_2$. The organic layer was separated, dried, filtered and the solvent was evaporated. The residue (3.3 g) was purified by column chromatography over silica gel (eluent: CH$_2$Cl$_2$/ CH$_3$OH/NH$_4$OH 95/5/0.2; 15–40 μm). Two pure fractions were collected and their solvents were evaporated. Fraction 1 was crystallized from 2-butanone and diethyl ether. The precipitate was filtered off and dried, yielding 0.6 g (A)-N-[4-[1-(1H-imidazol-1-yl)-3-methoxy-2-methylpropyl] phenyl]-2-benzothiazolamine (comp. 86).

EXAMPLE B-11

NaBH$_3$CN (0.009 mol) was added portionwise at −4° C. under N$_2$ flow to a solution of intermediate 56 (0.009 mol) in methanol (100 ml). The mixture was stirred for 1 hour, then poured out into K$_2$CO$_3$ 10% and ice and extracted with CH$_2$Cl$_2$. The organic layer was separated, dried, filtered and the solvent was evaporated. The residue was purified by column chromatography over silica gel (eluent: CH$_2$Cl$_2$/CH$_3$OH/NH$_4$OH 95.5/4.5/0.2 to 93/7/0.3; 15–40 μm). Two pure fractions were collected and their solvents were evaporated. The residue was crystallized from 2-butanone. The precipitate was filtered off, washed with diethyl ether and dried, yielding 0.61 g (B)-N-[4-[2-(dimethylamino)-1-(1-methyl-1H-imidazol-5-yl)propyl]phenyl)-2-benzothiazolamine (18%) (comp. 109).

EXAMPLE B-12

SnCl$_2$ (0.156 mol) and HCl 12N (0.562 mol) were added to a mixture of compound 126 (0.039 mol) in acetic acid (159 ml). The mixture was stirred and refluxed overnight, then poured out on ice, basified with a concentrated NH$_4$OH solution and extracted with CH$_2$Cl$_2$. The organic layer was separated, filtered over celite, dried, filtered and the solvent was evaporated. The residue was purified by column chromatography over silica gel (eluent: CH$_2$Cl$_2$/CH$_3$OH/NH$_4$OH 97.5/2.5/0.2; 15–40 μm). The pure fractions were collected and the solvent was evaporated. The residue was crystallized from 2-propanone and diethyl ether. The precipitate was filtered off and dried, yielding 1.19 g (8%) (±)-N-[4-[2-ethyl-1-(1-methyl-1H-imidazol-2-yl)butyl]phenyl]-2-benzothiazolamine (comp. 110).

EXAMPLE B-13

Compound 34 (0.0053 mol) was dissolved in boiling ethyl acetate (15 ml). H$_3$PO$_4$, (85%; 2.5 ml) was added dropwise while stirring. An oily precipitation resulted. The supernatant was removed by decantation, and 2-propanone (20 ml) was poured onto the residual oil. The mixture was stirred vigorously. The precipitate was filtered off and dried, yielding 3.0 g (82%) (B)-N-[4-[2-ethyl-1-(1H-1,2,4-triazol-1-yl) butyl]phenyl]-2-benzothiazolamine monohydrate phosphate (1:3) (comp. 87).

EXAMPLE B-14

A mixture of intermediate (26) (0.156 mol), 1H-1,2,4-triazole (0.313 mol) and K$_2$CO$_3$ (0.313 mol) in CH$_3$CN (800 ml) was stirred and refluxed for 12 hours. The solvent was evaporated. The residue was taken up in CH$_2$Cl$_2$/H$_2$O. The organic layer was separated, dried, filtered and the solvent was evaporated. The residue was purified by column chromatography over silica gel (eluent: CH$_2$Cl$_2$/CH$_3$OH/NH$_4$OH 98/2/0.1). The pure fractions were collected and the solvent was evaporated. The residue was crystallized from diethyl ether. The precipitate was filtered off and dried, yielding 16.8 g (±)-N-[4-[2-ethyl-1-(1H-1,2,4-triazol-1-yl) butyl]phenyl]-2-benzothiazolamine (26%) (comp. 25).

EXAMPLE B-15 n-Butyl lithium (1.6 M; 0.0607 mol) was added dropwise at −70° C. under N$_2$ flow to a solution of 1-methyl-1H-imidazole (0.0607 mol) in THF (60 ml). The mixture was stirred at −70° C. for 30 minutes. A mixture of intermediate 24 (0.0243 mol) in THF (60 ml) was added dropwise. The mixture was stirred and poured out into water and NH$_4$Cl. The organic layer was separated, dried, filtered and the solvent was evaporated. The residue was purified by column chromatography over silica gel (eluent: CH$_2$Cl$_2$/CH$_3$OH/NH$_4$OH 98/2/0.2). Two pure fractions were collected and their solvents were evaporated. The residue was crystallized from diethyl ether and methylethylketon. The precipitate was filtered off and dried, yielding 2.4 g (24%) (A)-α-[4-(2-benzothiazolylamino)phenyl]-α-[1-(dimethylamino) ethyl]-1-methyl-1H-imidazole-2-methanol (comp. 127) and 0.66 g (6%) (B)-α-[4-(2-benzothiazolylamino)-phenyl]-α-[1-(dimethylamino)ethyl]-1-methyl-1H-imidazole-2-methanol (comp. 128).

EXAMPLE B-16

(A)-α-[4-(2-benzothiazolylamino)phenyl]-α-[1-(dimethylamino)ethyl]-1-methyl-1H-imidazole-5-methanol (comp. 130) was prepared in a similar way as described in example B-15 with the exception that chlorotriethylsilane (equimolar with 1-methyl-1H-imidazole) is added to the reaction mixture prior to the addition of intermediate 24.

EXAMPLE B-17

A mixture of intermediate 19b (0.0409 mol) in 1-methyl-2-pyrrolidinone (40 ml) was added dropwise to a solution of amino-propanedinitrile (0.045 mol) in 1-methyl-2-pyrrolidinone (100 ml). The mixture was stirred at RT for 15 hours, then poured out into water and extracted with EtOAc. The organic layer was separated, dried, filtered and the solvent was evaporated. The residue was purified by column chromatography over silica gel (eluent: CH$_2$Cl$_2$/CH$_3$OH/NH$_4$OH 97/3/0.1). The pure fractions were collected and the solvent was evaporated. The residue was crystallized from methylethylketon and diethyl ether. The precipitate was filtered off and dried, yielding 0.96 g (±)-5-amino-2-[[4-[2-ethyl-1-(1H-1,2,4-triazol-1-yl)butyl]phenyl]amino-4-thiazolecarbonitrile (comp. 113).

Tables 1 to 6 list compounds of formula (I) that were prepared according to one of the above examples.

TABLE 1

[Structure: R⁹ᵃ-substituted benzothiazole-N(R³)-phenyl-CH(R²)-imidazole]

| Co. No. | Ex. No. | R² | R³ | R⁹ᵃ | Physical data |
|---|---|---|---|---|---|
| 1 | B.4.a | CH(CH₃)N(CH₃)₂ | H | H | (±)-(A) |
| 2 | B.4.a or B.5.a | CH(CH₃)N(CH₃)₂ | H | H | (±)-(B) |
| 3 | B.4.b | CH(CH₃)N(CH₃)₂ | H | H | (B1) |
| 4 | B.4.b | CH(CH₃)N(CH₃)₂ | H | H | (B2) |
| 5 | B.5.a | 3-fluorophenyl | H | H | (±) |
| 6 | B.5.a | CH₃ | H | H | (±) |
| 7 | B.5.a | phenyl | H | H | (±) |
| 8 | B.5.a | cyclohexyl | H | H | (±) |
| 9 | B.5.a | 4-fluorophenyl | H | H | (±) |
| 10 | B.5.a | CH(CH₃)N(CH₃)(C₂H₅) | H | H | (±) |
| 11 | B.5.a | CH(CH₃)COOC₂H₅ | H | H | (±) |
| 12 | B.5.a | CH(C₂H₅)N(CH₃)₂ | H | H | (±)-(A) |
| 13 | B.5.a | CH(C₂H₅)N(CH₃)₂ | H | H | (±)-(B) |
| 14 | B.5.a | CH(CH₃)—O-phenyl | H | H | (±)-(A) |
| 15 | B.5.a | C(CH₃)₂N(CH₃)₂ | H | H | (±) |
| 16 | B.3.a or B.4.a | CH(CH₃)₂ | H | H | (±) |
| 17 | B.4.a | CH(C₂H₅)₂ | H | 6-OCH₃ | (±) |
| 18 | B.4.a | CH(C₂H₅)₂ | H | H | (±) |
| 19 | B.3.c | CH(CH₃)N(CH₃)₂ | CH₃ | H | (±)-(B) |
| 20 | B.3.a + b | CH(CH₃)N(CH₃)₂ | H | 6-OC₂H₅ | (±)-(A) |
| 21 | B.3.a + b | CH(CH₃)N(CH₃)₂ | H | 5-CF₃ | (±)-(B) |
| 22 | B.3.a + b | CH(CH₃)N(CH₃)₂ | H | 5-CF₃ | (±)-(A) |
| 24 | B.1 | H | H | H | — |
| 59 | B.13 | CH(CH₃)N(CH₃)₂ | H | H | (B1)/HBr (1:2)/H₂O (1:1) |
| 60 | B.13 | CH(C₂H₅)₂ | H | H | HBr (1:2)/H₂O (1:1) |
| 61 | B.3.a | CH(CH₃)N(CH₃)₂ | H | 6-OC₂H₅ | (B) |
| 62 | B.3.b | C(CH₃)₂N(CH₃)₂ | H | H | (A) |
| 63 | B.3.b | C(CH₃)₂N(CH₃)₂ | H | H | (B) |
| 64 | B.5.a | CH(CH₃)N(CH₃)(CH₂—φ) | H | H | (A) |
| 65 | B.5.a | morpholin-N-CH(CH₃)— | H | H | (B) |
| 66 | B.3.a | CH(CH₃)N(CH₃)₂ | H | 6-F | (A) |
| 67 | B.3.a | CH(CH₃)N(CH₃)₂ | H | 6-CH₃ | (B) |
| 68 | B.3.a | CH(CH₃)N(CH₃)₂ | H | 6-F | (B) |
| 69 | B.3.a | CH(CH₃)N(CH₃)₂ | H | 6-CH₃ | (A) |
| 70 | B.5.a | piperidin-N-CH(CH₃)— | H | H | (A) |
| 71 | B.5.b | CH(CH₃)—CH₂OH | H | H | (A + B) |
| 72 | B.5.a | morpholin-N-CH(CH₃)— | H | H | (A) |
| 73 | B.3.a | CH(CH₃)N(CH₃)₂ | H | 6-OCH₃ | (A) |
| 74 | B.3.a | CH(CH₃)N(CH₃)₂ | H | 6-Cl | (A) |
| 75 | B.3.a | CH(CH₃)N(CH₃)₂ | H | 6-OCH₃ | (B) |
| 76 | B.14 | CH(CH₃)N(C₂H₅)₂ | H | H | (A) |
| 77 | B.3.a | CH(CH₃)N(CH₃)₂ | H | 6-Cl | (B) |
| 78 | B.3.b | CH(C₂H₅)N(CH₃)₂ | H | H | (B1); mp. 236° C. |
| 79 | B.3.b | CH(C₂H₅)N(CH₃)₂ | H | H | (B2) |
| 80 | B.5.a | 4-methylpiperazin-N-CH(CH₃)— | H | H | (A) |

TABLE 1-continued

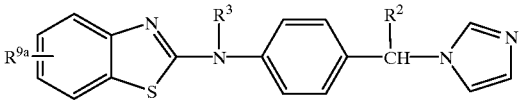

| Co. No. | Ex. No. | R² | R³ | R⁹ᵃ | Physical data |
|---|---|---|---|---|---|
| 81 | B.5.a | 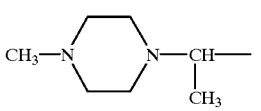 | H | H | (B) |
| 82 | B.5.b | 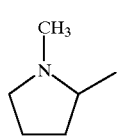 | H | H | (A) |
| 83 | B.5.b | 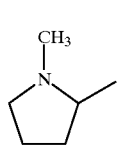 | H | H | (B) |
| 84 | B.5.a | 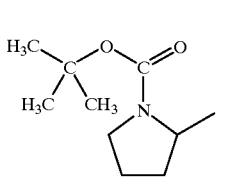 | H | H | (A) |
| 85 | B.5.a | 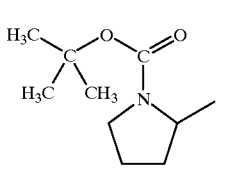 | H | H | (B) |
| 86 | B.10 | CH(CH₃)CH₂OCH₃ | H | H | (A) |

TABLE 2

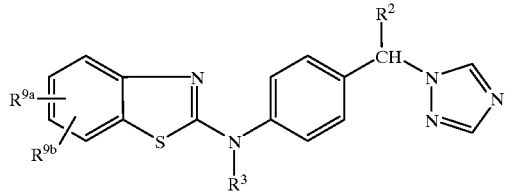

| Co. No. | Ex. No. | R² | R³ | R⁹ᵃ | R⁹ᵇ | Physical data |
|---|---|---|---|---|---|---|
| 25 | B.3.a; B.4.a or B.14 | CH(C₂H₅)₂ | H | H | H | (±) |
| 26 | B.4.a | CH(CH₃)N(CH₃)₂ | H | H | H | (±)-(A) |
| 27 | B.4.a | CH(CH₃)N(CH₃)₂ | H | H | H | (±)-(B) |
| 28 | B.4.b | CH(CH₃)N(CH₃)₂ | H | H | H | (B1) |
| 29 | B.4.b | CH(CH₃)N(CH₃)₂ | H | H | H | (B2) |
| 30 | B.4.a | CH(C₂H₅)₂ | H | 5-OCH₃ | 6-OCH₃ | (±) |
| 31 | B.4.a | CH(C₂H₅)₂ | H | 6-OCH₃ | H | (±) |
| 32 | B.3.c | CH(C₂H₅)₂ | CH₃ | H | H | (±) |
| 33 | B.3.b | CH(C₂H₅)₂ | H | H | H | (A) |
| 34 | B.3.b | CH(C₂H₅)₂ | H | H | H | (B); mp. 138° C. |
| 35 | B.3.b | CH(C₂H₅)₂ | H | H | H | (B); (E)-2-butenedioate (2:3) |
| 36 | B.3.a | 4-fluorophenyl | H | H | H | (±) |

TABLE 2-continued

[Structure: R^9a and R^9b substituted benzothiazole connected via N(R^3) to phenyl-CH(R^2)-triazole]

| Co. No. | Ex. No. | R² | R³ | R⁹ᵃ | R⁹ᵇ | Physical data |
|---------|---------|----|----|-----|-----|---------------|
| 37 | B.3.a | CH(CH₃)₂ | H | H | H | (±) |
| 38 | B.2 | C(CH₃)₂N(CH₃)₂ | H | H | H | (±) |
| 39 | B.2 | H | H | H | H | — |
| 40 | B.1 | cyclohexyl | H | H | H | (±) |
| 41 | B.1 | CH₃ | H | H | H | (±) |
| 42 | B.1 | 3-fluorophenyl | H | H | H | (±) |
| 43 | B.1 | phenyl | H | H | H | (±) |
| 87 | B.13 | CH(C₂H₅)₂ | H | H | H | (B); hydrate (1:1) phosphate (1:3) |

TABLE 3

[Structure: A-ring-C(=N)-NH-phenyl-CH(R²)-imidazole]

| Co. No. | Ex. No. | R² | A=N ring | Physical data |
|---------|---------|----|----|---------------|
| 44 | B.5.a | CH(C₂H₅)₂ | thiazolo[5,4-b]pyridin-2-yl | (±) |
| 45 | B.4.a | CH(CH₃)₂ | benzimidazol-2-yl (NH) | (±); mp. 228.7° C. |
| 46 | B.5.a | CH(C₂H₅)₂ | benzoxazol-2-yl | (±) |
| 47 | B.5.a | CH(CH₃)₂ | benzoxazol-2-yl | (±); mp. 173.6° C. |
| 48 | B.6 | H | 5-nitro-2-methylthiazol-2-yl | mp. >300° C. |

TABLE 3-continued
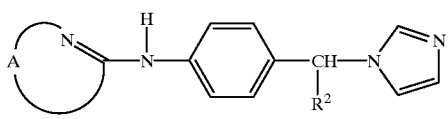
| Co. No. | Ex. No. | R² | | Physical data |
|---|---|---|---|---|
| 49 | B.7 | CH(CH₃)₂ | 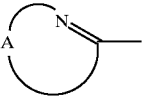 | (±); mp. 205.4° C. |
| 50 | B.7 | CH(CH₃)₂ | 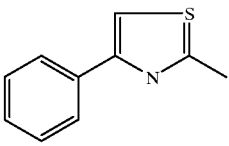 | (±); mp. 174.7° C. |
| 51 | B.8 | CH(CH₃)₂ | 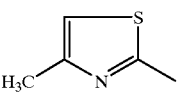 | (±); mp. 150.9° C. |
| 52 | B.5.a | CH(CH₃)₂ | 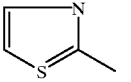 | (±) |
| 53 | B.5.a | CH(CH₃)₂ | 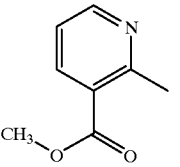 | (±); mp. 188.5° C. |
| 54 | B.5.b | CH(CH₃)₂ | 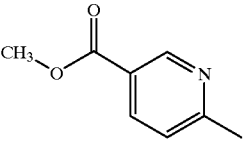 | (±) |
| 55 | B.5.c | CH(CH₃)₂ | 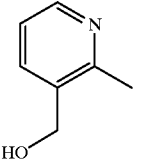 | (±) |
| 88 | B.5.a | CH(C₂H₅)₂ | 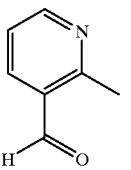 | — |

TABLE 3-continued

[Structure: A-N=... N(H)-C6H4-CH(R2)-imidazole ; and A-N=C(CH3) fragment]

| Co. No. | Ex. No. | R² | (heterocycle) | Physical data |
|---|---|---|---|---|
| 89 | B.1 | CH(C₂H₅)₂ | 1-methylisoquinoline | — |
| 90 | B.5.a | CH(C₂H₅)₂ | 4-methylpyrimidine | nitrate (1:1) |
| 91 | B.3.b | CH(C₂H₅)₂ | 2-methylbenzoxazole | (A); mp. 145° C. |
| 92 | B.3.b | CH(C₂H₅)₂ | 2-methylbenzoxazole | (B); mp. 170° C. |
| 93 | B.5.a | CH(C₂H₅)₂ | 2-methylquinoline | mp. 212° C. |
| 94 | B.5.a | CH(C₂H₅)₂ | 4-methyl-2-phenylquinazoline | — |
| 95 | B.5.a | CH(C₂H₅)₂ | 2-methylpyrimidine | — |
| 96 | B.5.a | CH(C₂H₅)₂ | 4-methyl-2-(methylthio)pyrimidine | — |
| 97 | B.5.a | CH(C₂H₅)₂ | 3,6-dimethylpyridazine | — |

TABLE 3-continued

| Co. No. | Ex. No. | R² | [Het group] | Physical data |
|---|---|---|---|---|
| 98 | B.5.a | CH(C₂H₅)₂ | 7H-purin-6-yl | HCl (1:2) |
| 99 | B.5.a | CH(C₂H₅)₂ | 3-methylpyridin-4-yl | — |
| 100 | B.5.a | CH(C₂H₅)₂ | phthalazin-1-yl | — |
| 101 | B.17 | CH(C₂H₅)₂ | 5-amino-4-cyano-2-methylthiazol-... | — |

TABLE 4

| Co. No. | Ex. No. | [A ring] | R² | Het | Physical data |
|---|---|---|---|---|---|
| 56 | B.6 | benzoxazol-2-yl | CH(C₂H₅)₂ | 1,2,4-triazol-1-yl | (±) |
| 57 | B.1 | benzothiazol-2-yl | H | 1,2,4-triazol-1-yl | — |

TABLE 4-continued

| Co. No. | Ex. No. | A-N= (structure) | R² | Het | Physical data |
|---|---|---|---|---|---|
| 58 | B.2 | thiazolo[5,4-b]pyridin-2-yl | CH(C₂H₅)₂ | 1-methyl-1,2,4-triazol-5-yl | (±) |
| 102 | B.1 | isoquinolin-1-yl | CH(C₂H₅)₂ | 1-methyl-1,2,4-triazol-5-yl | — |
| 103 | B.1 | pyrimidin-4-yl | CH(C₂H₅)₂ | 1-methyl-1,2,4-triazol-5-yl | — |
| 104 | B.1 | quinoxalin-2-yl | CH(C₂H₅)₂ | 1-methyl-1,2,4-triazol-5-yl | — |
| 105 | B.2 | pyrimidin-2-yl | CH(C₂H₅)₂ | 1-methyl-1,2,4-triazol-5-yl | — |
| 106 | B.2 | 2-phenylquinazolin-4-yl | CH(C₂H₅)₂ | 1-methyl-1,2,4-triazol-5-yl | — |
| 107 | B.2 | quinolin-2-yl | CH(C₂H₅)₂ | 1-methyl-1,2,4-triazol-5-yl | — |
| 108 | B11 | benzothiazol-2-yl | CH(CH₃)N(CH₅)₂ | 1,5-dimethylimidazol-2-yl | (A) |
| 109 | B11 | benzothiazol-2-yl | CH(CH₃)N(CH₅)₂ | 1,5-dimethylimidazol-2-yl | (B) |

TABLE 4-continued
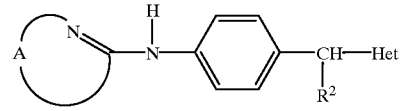
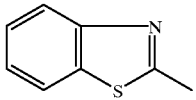
| Co. No. | Ex. No. | | R² | Het | Physical data |
|---|---|---|---|---|---|
| 110 | B12 | 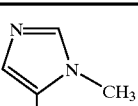 | CH(C₂H₅)₂ | 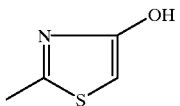 | (±) |
| 111 | B.7 | 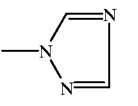 | CH(C₂H₅)₂ | 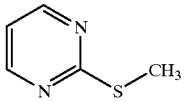 | — |
| 112 | B.2 | 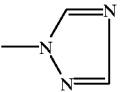 | CH(C₂H₅)₂ | 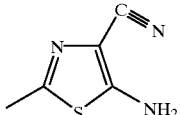 | — |
| 113 | B17 | 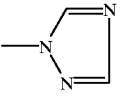 | CH(C₂H₅)₂ | 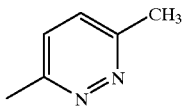 | (±) |
| 114 | B14 | 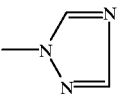 | CH(C₂H₅)₂ | 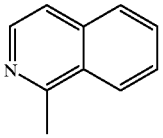 | — |
| 115 | B.1 | 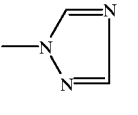 | CH(C₂H₅)₂ | 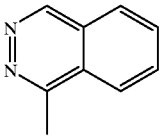 | — |
| 116 | B.1 | 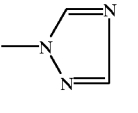 | CH(C₂H₅)₂ | 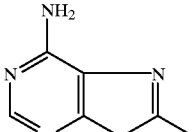 | — |
| 117 | B.9 | 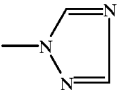 | CH(C₂H₅)₂ | | (±) |

TABLE 5

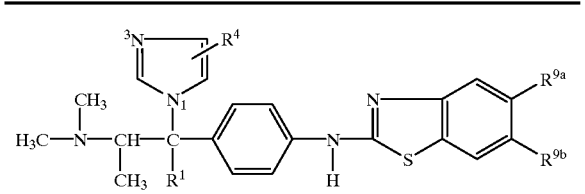

| Co. No. | Ex. No. | R¹ | R⁴ | R⁹ᵃ | R⁹ᵇ | Physical data |
|---|---|---|---|---|---|---|
| 118 | B.3.a | H | H | OCH₃ | OCH₃ | (A) |
| 119 | B.3.a | H | H | OCH₃ | OCH₃ | (B) |
| 120 | B.3.a | H | H | CH₃ | CH₃ | (A) |
| 121 | B.3.a | H | H | CH₃ | CH₃ | (B) |
| 122 | B.5.a | CH₃ | H | H | H | — |
| 123 | B.1 | H | 4-phenyl | H | H | (A)/HCl (1:2)/H₂O (1:2) |
| 124 | B.1 | H | 4-CH₃ | H | H | (A) |
| 125 | B.14 | H | 2-CH₃ | H | H | (A) |

TABLE 6

| Co. No. | Ex. No. | R² | Het | Physical data |
|---|---|---|---|---|
| 126 | B.15 | CH(C₂H₅)₂ | N=\\—N-CH₃ (imidazole) | (±) |
| 127 | B.15 | CH(CH₃)N(CH₅)₂ | N=\\—N-CH₃ (imidazole) | (A) |
| 128 | B.15 | CH(CH₃)N(CH₅)₂ | N=\\—N-CH₃ (imidazole) | (B) |
| 129 | B.16 | CH(C₂H₅)₂ | N=\\—N-CH₃ (imidazole) | — |
| 130 | B.16 | CH(CH₃)N(CH₅)₂ | N=\\—N-CH₃ (imidazole) | (A) |

TABLE 6-continued

| Co. No. | Ex. No. | R² | Het | Physical data |
|---|---|---|---|---|
| 131 | B.15 | CH(CH₃)N(CH₅)₂ | 3-methylpyridine | (A) |

Table 7 lists both the experimental (column heading "exp") and theoretical (column heading "theor") elemental analysis values for carbon, hydrogen and nitrogen of the compounds as prepared in the experimental part hereinabove.

TABLE 7

| Comp. No. | Carbon exp | Carbon theor | Hydrogen exp | Hydrogen theor | Nitrogen exp | Nitrogen theor |
|---|---|---|---|---|---|---|
| 5 | 68.85 | 68.98 | 4.64 | 4.28 | 13.43 | 13.99 |
| 7 | 70.09 | 72.23 | 4.54 | 4.74 | 14.21 | 14.65 |
| 8 | 69.45 | 71.10 | 6.14 | 6.23 | 14.33 | 14.42 |
| 9 | 68.43 | 68.98 | 4.42 | 4.28 | 13.64 | 13.99 |
| 10 | 67.35 | 67.49 | 6.51 | 6.44 | 17.57 | 17.89 |
| 11 | 63.89 | 65.00 | 5.34 | 5.45 | 13.50 | 13.78 |
| 12 | 67.46 | 67.49 | 6.21 | 6.44 | 17.87 | 17.89 |
| 13 | 67.70 | 67.49 | 6.56 | 6.44 | 18.16 | 17.89 |
| 14 | 68.66 | 70.40 | 5.18 | 5.20 | 12.77 | 13.14 |
| 16 | 69.13 | 68.94 | 5.52 | 5.78 | 15.77 | 16.08 |
| 19 | 67.64 | 67.49 | 6.52 | 6.44 | 18.10 | 17.89 |
| 21 | 59.26 | 59.31 | 5.13 | 4.98 | 15.42 | 15.72 |
| 22 | 59.12 | 59.31 | 5.07 | 4.98 | 15.50 | 15.72 |
| 25 | 66.72 | 66.81 | 6.11 | 6.14 | 18.50 | 18.55 |
| 28 | 63.08 | 63.47 | 6.04 | 5.86 | 21.92 | 22.20 |
| 29 | 62.56 | 63.47 | 6.04 | 5.86 | 21.53 | 22.20 |
| 30 | 62.60 | 63.13 | 6.10 | 6.22 | 15.25 | 16.01 |
| 31 | 64.89 | 64.84 | 6.11 | 6.18 | 16.77 | 17.18 |
| 27 | 62.85 | 63.47 | 5.68 | 5.86 | 21.86 | 22.20 |
| 33 | 66.64 | 66.81 | 6.32 | 6.14 | 18.37 | 18.55 |
| 34 | 67.47 | 66.81 | 6.18 | 6.14 | 17.87 | 18.55 |
| 35 | 58.31 | 58.79 | 5.04 | 5.30 | 12.37 | 12.70 |
| 38 | 64.23 | 64.26 | 6.01 | 6.16 | 21.46 | 21.41 |
| 39 | 61.01 | 62.52 | 4.31 | 4.26 | 22.04 | 22.78 |
| 40 | 66.82 | 67.84 | 5.81 | 5.95 | 17.80 | 17.98 |
| 41 | 62.31 | 63.53 | 4.62 | 4.70 | 21.25 | 21.79 |
| 43 | 69.00 | 68.91 | 4.42 | 4.47 | 18.44 | 18.26 |
| 47 | 69.79 | 72.27 | 6.19 | 6.06 | 16.15 | 16.85 |
| 51 | 64.30 | 64.40 | 6.07 | 6.08 | 18.67 | 18.78 |
| 57 | 62.65 | 62.52 | 4.35 | 4.26 | 22.56 | 22.78 |

C. Pharmacological examples

EXAMPLE C.1

Inhibition of Retinoic A (RA) Metabolism

MCF-7 human breast cancer cells were grown as stock cultures according to art-known protocols. One day before the experiment, RA is added to the stock cultures to stimulate RA-metabolism. At the start of the experiment, cell suspensions were incubated in a tissue culture medium containing ³H-RA as the substrate. Different concentrations of the test compound (dissolved in 1% DMSO) were added to the incubation mixtures, and at the end of the incubation, the unmetabolized RA is separated from its polar metabolites. The fraction containing the polar $^3$H-labelled metabolites was collected and counted in a scintillation counter. For each experiment, a control and a blank incubation were run in parallel. Those compounds that were tested, i.e. compound numbers 1–4, 8, 10, 16–18, 24, 25, 27, 29–31, 33, 34, 35, 37, 40, 44–47, 49–51, 53, 56 and 58, all had an $IC_{50}$ value of lower than $1\times10^{-8}$ M whereby an $IC_{50}$ value is defined as the concentration needed to reduce the amount of metabolites to 50% of the control.

EXAMPLE C.2

"Vaginal Keratinization Test on Ovariectomized Rats"

Ovariectomized rats were injected subcutaneously with a sesame oil solution containing 100 μg of estradiol undecylate in a volume of 0.1 ml per 100 g body weight and control animals were injected with sesame oil. On day one, two and three, test animals were treated once daily with a per os dose of the test compound and control animals with the drug vehicle (PEG 200). One day after the last treatment, the animals were sacrificed and their vaginas were processed for histological evaluation according to the method described in J. Pharmacol. Exp. Ther. 261(2), 773–779 (1992). A dose at which 50% of the tested rats show complete suppression of the estradiol undecylate induced keratinization effects is defined as an active dose. The compound numbers 2–5, 8, 15–19, 25, 27–29, 31, 32, 34, 42, 46 and 56 all had a lowest active dose (LAD) equal to or lower than 2.5 mg/kg. Other compounds that were tested had a LAD higher than 2.5 mg/kg.

D. Composition examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable acid addition salt thereof.

EXAMPLE D.1

Oral Solution 9 g of methyl 4-hydroxybenzoate and 1 g of propyl 4hydroxy-benzoate were dissolved in 4 l of boiling purified water. In 3 l of this solution were dissolved first 10 g of 2,3-dihydroxybutanedioic acid and thereafter 20 g of A.I. The latter solution was combined with the remaining part of the former solution and 12 l 1,2,3-propane-triol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of A.I. per teaspoonful (5 ml). The resulting solution was filled in suitable containers.

EXAMPLE D.2

Oral Drops 500 g of the A.I. was dissolved in 0.5 l of 2-hydroxypropanoic acid and 1.5 l of the polyethylene glycol at 60~80° C. After cooling to 30~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE D.3

Capsules 20 g of A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 20 mg of A.I.

EXAMPLE D.4

Injectable Solution 0.5 mg A.I. 1, 50 mg glucose anhydrous and 0.332 ml concentrated hydrochloric acid were mixed with 0.8 ml water for injections. Sodium hydroxide was added until pH=3.2±0.1 and water was added to 1 ml. The solution was sterilized and filled in sterile containers.

EXAMPLE D.5

Film-coated Tablets

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10.000 tablets, each comprising 10 mg of the active ingredient.

Coating

To a solution of 10 g methyl cellulose (Methocel 60 HG ®) in 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension (Opaspray K-1-2109 ®) and the whole was homogenated. The tablet cores were coated with the thus obtained mixture in a coating apparatus.

EXAMPLE D.6

2% Cream 75 mg stearyl alcohol, 2 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70 to 75° C. while using a homogenizer for liquids. The resulting emulsion is allowed to cool to below 25° C. while continuously mixing. A solution of 20 mg A.I., 1 mg polysorbate 80 and purified water and a solution of 2 mg sodium sulfite anhydrous in purified water are next added to the emulsion while continuously mixing. The cream, 1 g of the A.I. is homogenized and filled into suitable tubes.

EXAMPLE D.7

2% Topical Gel

To a solution of 200 mg hydroxypropyl b-cyclodextrine in purified water is added 20 mg of A.I. while stirring. Hydrochloric acid is added until complete dissolution and then sodium hydroxide is added until pH 6.0. This solution is added to a dispersion of 10 mg carrageenan PJ in 50 mg propylene glycol while mixing. While mixing slowly, the mixture is heated to 50° C. and allowed to cool to about 35° C. whereupon 50 mg ethyl alcohol 95% (v/v) is added. The rest of the purified water q.s. ad 1 g is added and the mixture is mixed to homogenous.

EXAMPLE D.8

2% Topical Cream

To a solution of 200 mg hydroxypropyl b-cyclodextrine in purified water is added 20 mg of A.I. while stirring. Hydrochloric acid is added until complete dissolution and next sodium hydroxide is added until pH 6.0. While stirring, 50 mg glycerol and 35 mg polysorbate 60 are added and the mixture is heated to 70° C. The resulting mixture is added to a mixture of 100 mg mineral oil, 20 mg stearyl alcohol, 20 mg cetyl alcohol, 20 mg glycerol monostearate and 15 mg sorbate 60 having a temperature of 70° C. while mixing slowly. After cooling down to below 25° C., the rest of the purified water q.s. ad 1 g is added and the mixture is mixed to homogenous.

EXAMPLE D.9

2% Liposome Formulation

A mixture of 2 g A.I. microfine, 20 g phosphatidyl choline, 5 g cholesterol and 10 g ethyl alcohol is stirred and heated at 55–60° C. until complete dissolution and is added to a solution of 0.2 g methyl paraben, 0.02 g propyl paraben, 0.15 g disodium edetate and 0.3 g sodium chloride in purified water while homogenizing. 0.15 g Hydroxypropylmethylcellulose in purified water ad 100 g is added and the mixing is continued until swelling is complete.

What is claimed is:

1. A compound of formula

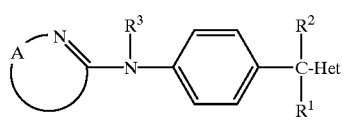

(I)

a N-oxide, a pharmaceutically acceptable addition salt or a stereochemically isomeric form thereof, wherein:

$R^1$ represents hydrogen, hydroxy, $C_{1-6}$alkyl or aryl;

$R^2$ represents hydrogen; $C_{1-12}$alkyl; $C_{3-7}$cycloalkyl; $C_{2-8}$alkenyl; aryl; pyrrolidinyl optionally substituted with $C_{1-4}$alkyl or $C_{1-4}$alkyloxycarbonyl; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- and di(aryl) amino, aryl$C_{1-4}$alkylamino, ($C_{1-4}$alkyl) (aryl$C_{1-4}$alkyl) amino, pyrrolidinyl, piperidinyl, piperazinyl optionally substituted with $C_{1-4}$alkyl, morpholinyl, perhydroazepinyl, carboxyl, $C_{1-4}$alkyloxycarbonyl, aminocarbonyl, mono- and di($C_{1-4}$alkyl) aminocarbonyl, aryl, aryloxy and arylthio;

$R^3$ represents hydrogen, $C_{1-6}$alkyl, aryl or $C_{1-6}$alkyl substituted with aryl;

Het represents an unsaturated heterocycle selected from imidazolyl, triazolyl, and tetrazolyl; each of said unsaturated heterocycles may optionally be substituted with amino, mercapto, $C_{1-6}$alkyl, $C_{1-6}$alkylthio or aryl;

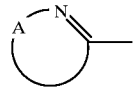

represents a radical of formula

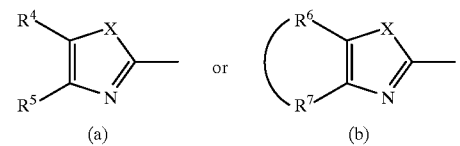

wherein each X independently represents S, S(=O) or $S(=O)_2$;

$R^4$ and $R^5$ each independently represent hydrogen, hydroxy, halo, cyano, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl;

—$R^6$—$R^7$— represents a bivalent radical of formula:

—$CR^9$=$CR^9$—$CR^9$=$CR^9$—    (b-1);

wherein each $R^9$ independently represents hydrogen, hydroxy, halo, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl; and aryl represents phenyl or phenyl substituted with one, two or three substituents selected from hydroxy, halo, cyano, amino, mono- or di($C_{1-6}$alkyl)amino, $C_{1-6}$alkyl, halo$C_{1-6}$alkyl, hydroxy$C_{1-6}$alkyl, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or halo$C_{1-12}$alkanediyl.

2. A compound according to claim 1, wherein $R^1$ represents hydrogen, $C_{1-6}$alkyl or aryl;

$R^2$ represents hydrogen; $C_{1-12}$alkyl; $C_{3-7}$cycloalkyl; $C_{2-8}$alkenyl; aryl; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- and di(aryl)amino, aryl$C_{1-4}$alkylamino, ($C_{1-4}$alkyl) (aryl$C_{1-4}$alkyl)amino, pyrrolidinyl, piperidinyl, piperazinyl, morpholinyl, perhydro-azepinyl, carboxyl, $C_{1-4}$alkyloxycarbonyl, aminocarbonyl, mono- and di($C_{1-4}$alkyl) aminocarbonyl, aryl, aryloxy and arylthio;

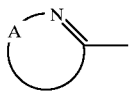

represents a radical of formula (a) or (b) wherein $R^4$ and $R^5$ each independently represent hydrogen, hydroxy, halo, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl.

3. A compound according to claim 1, wherein
$R^1$ represents hydrogen, hydroxy, $C_{1-6}$alkyl;
$R^2$ represents hydrogen; $C_{1-12}$alkyl; $C_{3-7}$cycloalkyl; pyrrolidinyl optionally substituted with $C_{1-4}$alkyl or $C_{1-4}$alkyloxycarbonyl; aryl or $C_{1-12}$alkyl substituted with one or two substituents selected from hydroxy, $C_{1-4}$alkyloxy, mono- and di($C_{1-4}$alkyl)amino, ($C_{1-4}$alkyl)(aryl$C_{1-4}$alkyl)amino, $C_{1-4}$alkyloxycarbonyl, morpholinyl, piperidinyl, piperazinyl optionally substituted with $C_{1-4}$alkyl, and aryloxy;
$R^3$ represents hydrogen and $C_{1-6}$alkyl;
Het represents imidazolyl optionally substituted with $C_{1-6}$alkyl; pyridinyl or triazolyl;

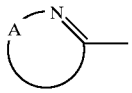

represents a radical of formula (a) or (b), wherein:
X represents S;
$R^4$ and $R^5$ each independently represent hydrogen, hydroxy, nitro, cyano, amino, $C_{1-6}$alkyl or aryl;
—$R^6$—$R^7$— represents a bivalent radical of formula (b-1), wherein each $R^9$ independently represents hydrogen, $C_{1-6}$alkyl, hydroxy, halo, amino, halo$C_{1-6}$alkyl or $C_{1-6}$-alkyloxy.

4. A compound according to claim 1, wherein Het is 1-imidazolyl optionally substituted with $C_{1-6}$alkyl or aryl; 2-imidazolyl optionally substituted with $C_{1-6}$alkyl; 5-imidazolyl optionally substituted with $C_{1-6}$alkyl; 1,3,4-triazol-1-yl and 1,2,4-triazol-1-yl.

5. A compound according to claim 1, wherein

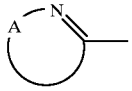

represents a radical of formula (b), wherein X represents S; and
—$R^6$—$R^7$— represents a bivalent radical of formula (b-1).

6. A compound according to claim 1, wherein $R^2$ represents $C_{1-12}$alkyl; $C_{3-7}$cycloalkyl; aryl or $C_{1-12}$alkyl substituted with mono- or di($C_{1-4}$alkyl)amino, $C_{1-4}$alkyloxycarbonyl or aryloxy.

7. A compound according to claim 1, wherein the compound is
N-[4-[2-ethyl-1(1H-imidazol-1-yl)butyl]phenyl]-2-benzothiazolamine;
N-[4-[2-ethyl-1-(1H-1,2,4-triazol-1-yl)butyl]phenyl]-2-benzothiazolamine;
N-[4-[2-(dimethylamino)-1-(1H-imidazol-1-yl)propyl]phenyl]-2-benzothiazolamine;
N-[4-[2-(dimethylamino)-1-(1H-1,2,4-triazol-1-yl)propyl]phenyl]-2-benzothiazolamine;
N-[4-[2-ethyl-1-(1H-imidazol-1-yl)butyl]phenyl]-6-methoxy-2-benzothiazolamine;
N-[4-[2-(dimethylamino)-1-(1H-imidazol-1-yl)-2-methylpropyl]phenyl]-2-benzothiazolamine;
N-[4-[2-(dimethylamino)-2-methyl-1-(1H-1,2,4-triazol-1-yl)propyl]phenyl]-2-benzothiazolamine;
N-[4-[cyclohexyl(1H-imidazol-1-yl)methyl]phenyl]-2-benzothiazolamine;
N-[4-[cyclohexyl(1H-1,2,4-triazol-1-yl)methyl]phenyl]-2-benzothiazolamine, a N-oxide, a stereochemically isomeric form or a pharmaceutically acceptable addition salt thereof.

8. A composition comprising a pharmaceutically acceptable carrier and, as active ingredient, a therapeutically effective amount of a compound as defined in claim 1.

9. A process of preparing a composition comprising intimately mixing a pharmaceutically acceptable carrier with a therapeutically effective amount of a compound as defined in claim 1.

10. A process of preparing a compound as claimed in claim 1, comprising a) reacting an intermediate of formula (II)

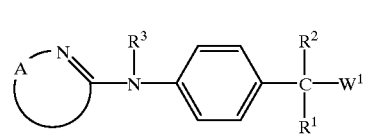

(II)

wherein $R^1$ to $R^3$ and

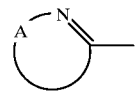

are defined as in claim 1, and $W^1$ is an appropriate leaving group, with Het-H (III) or a functional derivative thereof, wherein Het is defined as in claim 1, in a reaction-inert solvent and in the presence of a suitable base, and optionally, in the presence of triphenylphosphine and diethyl azodicarboxylate;

b) N-alkylation of an intermediate of formula (IV)

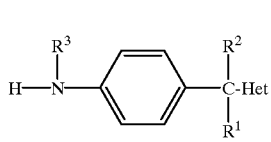

(IV)

wherein $R^1$ to $R^3$ and Het are defined as in claim 1, with an intermediate of formula (V)

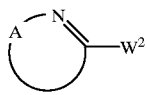

(V)

wherein

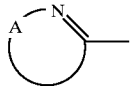

is defined as in claim 1 and $W^2$ is an appropriate leaving group, in a reaction-inert solvent;

c) reacting an intermediate of formula (VI)

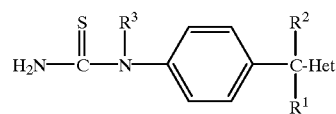

(VI)

wherein $R^1$ to $R^3$ and Het are defined as in claim 1, with an intermediate of formula (VII) or a functional derivative thereof,

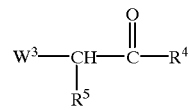

(VII)

wherein $R^4$ and $R^5$ are defined as in claim 1 and $W^3$ is an appropriate leaving group, in a reaction-inert solvent and optionally in the presence of an acid, thus forming a compound of formula (I-a-1)

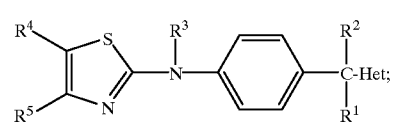

(I-a-1)

d) reacting an intermediate of formula (VIII)

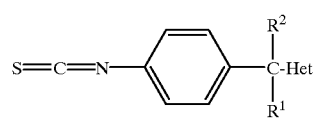

(VIII)

wherein $R^1$, $R^2$ and Het are defined as in claim 1, with an intermediate of formula (IX-1)

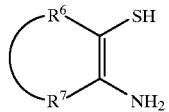

(IX-1)

wherein —$R^6$—$R^7$— is defined as in claim 1, in a reaction-inert solvent, thus forming an intermediate of formula (I-b-1)

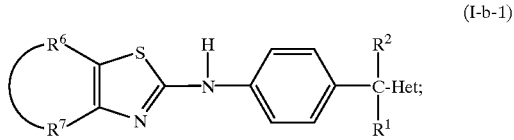

(I-b-1)

e) reacting an intermediate of formula (VIII)

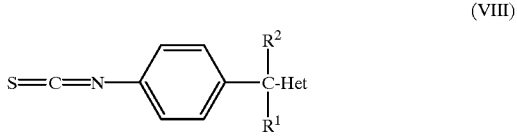

(VIII)

wherein $R^1$, $R^2$ and Het are defined as in claim 1, with an intermediate of formula (IX-2)

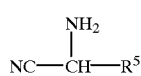

(IX-2)

wherein —$R^5$ is defined as in claim 1, in a reaction-inert solvent, thus forming an intermediate of formula (I-a-2)

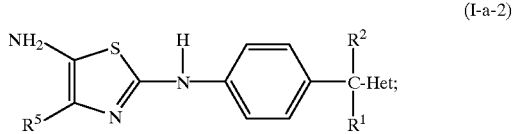

(I-a-2)

f) reacting an intermediate of formula (X)

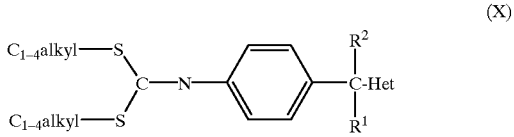

(X)

wherein $R^1$, $R^2$ and Het are defined as in claim 1, with an intermediate of formula (IX-1) in a reaction-inert solvent and in the presence of a suitable base, thus forming a compound of formula (I-b-1);

g) reacting an intermediate corresponding to a compound of formula (I) wherein $R^1$ and $R^2$ together with the carbon atom to which they are attached form a carbonyl group, with Het-H (III) whereby Het is defined as in claim 1, in the presence of an appropriate reagent, in a reaction-inert solvent, and optionally in the presence of chlorotriethylsilane, thus forming a compound of formula (I) wherein $R^1$ is hydroxy;

h) reacting an intermediate corresponding to a compound of formula (I) wherein $R^2$ is L-$C_{1-12}$alkyl wherein L is an appropriate leaving group, with $C_{1-4}$alkylO$^-$M$^+$ wherein M$^+$ is a suitable metal ion, in a suitable solvent, thus forming a compound of formula (I) wherein $R^2$ is $C_{1-4}$alkyloxy$C_{1-12}$alkyl;

i) reducing an intermediate corresponding to a compound of formula (I) wherein said $R^2$ is connected to the carbon atom bearing the $R_2$ substituent by a double bond using a suitable reducing agent, in a suitable solvent, thus forming a compound of formula (I) wherein $R^2$ is optionally substituted $C_{1-12}$alkyl;

and if desired, converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and also, if desired, preparing stereochemically isomeric forms or N-oxide forms thereof.

11. A method of treating a warm-blooded animal suffering from a disease characterized by an abnormal proliferation and/or abnormal differentiation of normal, preneoplastic or neoplastic cells comprising administering to the warm-blooded animal a retinoic mimetic amount of a compound of claim 1.

12. The method of claim 11, wherein the disease is selected from cancer or psoriasis.

* * * * *